United States Patent
Rahman et al.

(10) Patent No.: US 9,040,049 B2
(45) Date of Patent: May 26, 2015

(54) ADAM-15 ANTIBODIES AND IMMUNOGENIC PEPTIDES

(75) Inventors: Salman Rahman, London (GB); Yatin Patel, London (GB); Holger Gerhardt, London (GB); Andrea Emma Lundkvist, Malmo (SE)

(73) Assignee: Vasgen Limited, London (GB)

( * ) Notice: Subject to any disclaimer, the term of this patent is extended or adjusted under 35 U.S.C. 154(b) by 809 days.

(21) Appl. No.: 12/934,541

(22) PCT Filed: Mar. 24, 2009

(86) PCT No.: PCT/IB2009/005613
§ 371 (c)(1),
(2), (4) Date: Dec. 6, 2010

(87) PCT Pub. No.: WO2009/118660
PCT Pub. Date: Oct. 1, 2009

(65) Prior Publication Data
US 2011/0117090 A1      May 19, 2011

Related U.S. Application Data

(60) Provisional application No. 61/038,837, filed on Mar. 24, 2008.

(51) Int. Cl.
| | |
|---|---|
| A61K 39/00 | (2006.01) |
| A61K 39/395 | (2006.01) |
| A61K 39/40 | (2006.01) |
| A61K 49/00 | (2006.01) |
| C07K 16/40 | (2006.01) |
| C12N 15/113 | (2010.01) |

(52) U.S. Cl.
CPC ............ *C07K 16/40* (2013.01); *C12N 15/1137* (2013.01); *A61K 2039/505* (2013.01); *C07K 2299/00* (2013.01); *C07K 2316/96* (2013.01); *C12N 2310/14* (2013.01)

(58) Field of Classification Search
CPC .......... C07K 1/00; C07K 16/00; C07K 16/18; C07K 16/40; C07K 2299/00; C07K 2316/00; C07K 2317/00; C07K 2317/30; C07K 2317/34; A61K 6/00; A61K 39/00; A61K 2039/505
See application file for complete search history.

(56) References Cited

U.S. PATENT DOCUMENTS

| 6,344,352 B1 * | 2/2002 | Merkulov et al. ............ 435/219 |
| 2004/0102392 A1 | 5/2004 | Bennett et al. |

FOREIGN PATENT DOCUMENTS

| EP | 1 609 804 A1 | 12/2005 |
| EP | 2 174 956 A1 | 4/2010 |
| EP | 2 186 894 A1 | 5/2010 |
| WO | WO 02/066057 A2 | 8/2002 |
| WO | WO 2004/024089 A2 | 3/2004 |
| WO | WO 2009/101968 A1 | 8/2009 |
| WO | WO 2009/118660 A2 | 10/2009 |

OTHER PUBLICATIONS

Horiuchi et al. (Molecular and Cellular Biology 23(16): 5614-5624, Aug. 2003).*
Trochon, et al.; "Endothelial metalloprotease-disintegrin protein (ADAM) is implicated in angiogenesis in vitro"; Angiogenesis (1998); 2(3): 277-285.
Seals, et al.; "The ADAMs family of metalloproteases: multidomain proteins with multiple functions"; Genes & Development (2003); 17: 7-30.
Saunders, et al.; "Coregulation of vascular tube stabilization by endothelial cell TIMP-2 and pericyte TIMP-3"; J of Cell Biology (2006); 175(1): 179-191.
Roy, et al.; "Making the cut: Protease-mediated regulation of angiogenesis"; Experimental Cell Research (2006); 312: 608-622.
Najy, et al.; "ADAM15 Supports Prostate Cancer Metastasis by Modulating Tumor Cell-Endothelial Cell Interaction"; Cancer Res (2008); 68(4): 1092-1099.
Martin, et al.; "The Role of ADAM 15 in Glomerular Mesangial Cell Migration"; J of Biological Chemistry (2002); 277(37): 33683-33689.
Charrier-Hisamuddin, et al.; "ADAM-15: a metalloprotease that mediates inflammation"; The FASEB Journal (2008); 22: 641-653.
International Preliminary Report on Patentability for PCT/IB2009/005613 mailed Oct. 7, 2010.
International Search Report and Written Opinion for PCT/IB2011/002860 mailed Jul. 3, 2012.
Aktas et al., Aspirin induces platelet receptor shedding via ADAM17 (TACE). J Biol Chem. Dec. 2, 2005;280(48):39716-22. Epub Sep. 22, 2005.
Alfandari et al., ADAM 13 is a metalloprotease required for cranial neural crest-cell migration. Curr Biol. Jun. 26, 2001;11(12):918-30.
Alfandari et al., ADAM 13: a novel ADAM expressed in somitic mesoderm and neural crest cells during *Xenopus laevis* development. Dev Biol. Feb. 15, 1997;182(2):314-30.
Bajou et al., The plasminogen activator inhibitor PAI-1 controls in vivo tumor vascularization by interaction with proteases, not vitronectin. Implications for antiangiogenic strategies. J Cell Biol. Feb. 19, 2001;152(4):777-84.
Bass et al., Regulation of urokinase receptor proteolytic function by the tetraspanin CD82. J Biol Chem. Apr. 15, 2005;280(15):14811-8. Epub Jan. 27, 2005.

(Continued)

*Primary Examiner* — Alana Harris Dent
(74) *Attorney, Agent, or Firm* — Wolf, Greenfield & Sacks, P.C.

(57) ABSTRACT

The present invention relates to antibodies and antigen-binding fragments thereof, immunogenic peptide(s), and siRNA molecules which are capable of inhibiting neovascularization and/or angiogenesis and endothelial cell proliferation. The invention relates to antibodies and antigen-binding fragments thereof with specificity towards the metalloprotease domain of ADAM 15 and to immunogenic peptide(s) that elicits such antibodies. The invention also relates to compositions and kits comprising the antibodies and immunogenic peptide(s) of the invention, as well as methods and uses of the antibodies and antigen-binding fragments thereof and immunogenic peptide(s), as well as siRNA molecules.

7 Claims, 8 Drawing Sheets

(56) References Cited

OTHER PUBLICATIONS

Bellacosa et al., Activation of AKT kinases in cancer: implications for therapeutic targeting. Adv Cancer Res. 2005;94:29-86.
Blobel, ADAMs: key components in EGFR signalling and development. Nat Rev Mol Cell Biol. Jan. 2005;6(1):32-43.
Blobel, Metalloprotease-disintegrins: links to cell adhesion and cleavage of TNF alpha and Notch. Cell. Aug. 22, 1997;90(4):589-92.
Böhm et al., ADAM15 modulates outside-in signalling in chondrocyte-matrix interactions. J Cell Mol Med. Aug. 2009;13(8B):2634-44.
Busso et al., Extravascular Coagulation and the Plasminogen Activator/Plasmin System in Rheumatoid Arthritis. Arthritis & Rhematism. Sep. 2002;46(9):2268-79.
Carmeliet et al., Targeted deficiency or cytosolic truncation of the VE-cadherin gene in mice impairs VEGF-mediated endothelial survival and angiogenesis. Cell. Jul. 23, 1999;98(2):147-57.
Charrier et al., ADAM-15/metargidin mediates homotypic aggregation of human T lymphocytes and heterotypic interactions of T lymphocytes with intestinal epithelial cells. J Biol Chem. Jun. 8, 2007;282(23):16948-58.
Charrier-Hisamuddin et al.,. ADAM-15: a metalloprotease that mediates inflammation. FASEB J. Mar. 2008;22(3):641-53. Epub Sep. 28, 2007.
Chen et al., Akt1 regulates pathological angiogenesis, vascular maturation and permeability in vivo. Nat Med. Nov. 2005;11(11):1188-96. Epub Oct. 16, 2005.
Cirilli et al., 2 angstrom X-ray structure of adamalysin II complexed with a peptide phosphonate inhibitor adopting a retro-binding mode. FEBS Lett. Dec. 1, 1997;418(3):319-22.
Dance et al., The adaptor protein Gab1 couples the stimulation of vascular endothelial growth factor receptor-2 to the activation of phosphoinositide 3-kinase. J Biol Chem. Aug. 11, 2006;281(32):23285-95. Epub Jun. 20, 2006.
Davies et al., Microglia and macrophages are increased in response to ischemia-induced retinopathy in the mouse retina. Mol Vis. May 10, 2006;12:467-77.
Devy et al., New Strategies for the Next Generation of Matrix-Metalloproteinase Inhibitors: Selectively Targeting Membrane-Anchored MMPs with Therapeutic Antibodies. Biochem Res Int. 2011;2011:191670. doi: 10.1155/2011/191670. Epub Oct. 28, 2010.
Eto et al., RGD-independent binding of integrin alpha9beta1 to the ADAM-12 and -15 disintegrin domains mediates cell-cell interaction. J Biol Chem. Nov. 10, 2000;275(45):34922-30.
Fong et al., Role of the Flt-1 receptor tyrosine kinase in regulating the assembly of vascular endothelium. Nature. Jul. 6, 1995;376(6535):66-70.
Gerber et al., Vascular endothelial growth factor regulates endothelial cell survival through the phosphatidylinositol 3'-kinase/Akt signal transduction pathway. Requirement for Flk-1/KDR activation. J Biol Chem. Nov. 13, 1998;273(46):30336-43.
Gerhardt et al., VEGF guides angiogenic sprouting utilizing endothelial tip cell filopodia. J Cell Biol. Jun. 23, 2003;161(6):1163-77.
Gerhardt, How do endothelial cells orientate? EXS. 2005;(94):3-15.
Gomis-Rüth, Catalytic domain architecture of metzincin metalloproteases. J Biol Chem. Jun. 5, 2009;284(23):15353-7. doi: 10.1074/jbc.R800069200. Epub Feb. 5, 2009.
Ham et al., ADAM15 is an adherens junction molecule whose surface expression can be driven by VE-cadherin. Exp Cell Res. Oct. 1, 2002;279(2):239-47.
Herren et al., Expression of a disintegrin-like protein in cultured human vascular cells and in vivo. FASEB J. Feb. 1997;11(2):173-80.
Hiratsuka et al., Flt-1 lacking the tyrosine kinase domain is sufficient for normal development and angiogenesis in mice. Proc Natl Acad Sci U S A. Aug. 4, 1998;95(16):9349-54.
Ikenoue et al., Functional analysis of PIK3CA gene mutations in human colorectal cancer. Cancer Res. Jun. 1, 2005;65(11):4562-7.
Jiang et al., Astrocytes modulate retinal vasculogenesis: effects on fibronectin expression. J Cell Sci. Sep. 1994;107 ( Pt 9):2499-508.
Krätzschmar et al., Metargidin, a membrane-anchored metalloprotease-disintegrin protein with an RGD integrin binding sequence. J Biol Chem. Mar. 1, 1996;271(9):4593-6.
Laramée et al., The scaffolding adapter Gab1 mediates vascular endothelial growth factor signaling and is required for endothelial cell migration and capillary formation. J Biol Chem. Mar. 16, 2007;282(11):7758-69. Epub Dec. 17, 2006.
Lee et al., PIK3CA gene is frequently mutated in breast carcinomas and hepatocellular carcinomas. Oncogene. Feb. 17, 2005;24(8):1477-80.
Levine et al., Frequent mutation of the PIK3CA gene in ovarian and breast cancers. Clin Cancer Res. Apr. 15, 2005;11(8):2875-8.
Lunn et al., Purification of ADAM 10 from bovine spleen as a TNFalpha convertase. FEBS Lett. Jan. 6, 1997;400(3):333-5.
Maretzky et al., Characterization of the catalytic activity of the membrane-anchored metalloproteinase ADAM15 in cell-based assays. Biochem J. Apr. 28, 2009;420(1):105-13.
Martin et al., The role of ADAM 15 in glomerular mesangial cell migration. J Biol Chem. Sep. 13, 2002;277(37):33683-9. Epub Jun. 28, 2002.
Macri et al., Growth factor binding to the pericellular matrix and its importance in tissue engineering. Adv Drug Deliv Rev. Nov. 10, 2007;59(13):1366-81. Epub Aug. 16, 2007.
Mahabeleshwar et al., Integrin signaling is critical for pathological angiogenesis. J Exp Med. Oct. 30, 2006;203(11):2495-507. Epub Oct. 9, 2006.
Matsumoto et al., VEGF receptor-2 Y951 signaling and a role for the adapter molecule TSAd in tumor angiogenesis. EMBO J. Jul. 6, 2005;24(13):2342-53. Epub Jun. 16, 2005.
McGeehan et al., Regulation of tumour necrosis factor-alpha processing by a metalloproteinase inhibitor. Nature. Aug. 18, 1994;370(6490):558-61.
Miralem et al., VEGF(165) requires extracellular matrix components to induce mitogenic effects and migratory response in breast cancer cells. Oncogene. Sep. 6, 2001;20(39):5511-24.
Murphy, Fell-Muir Lecture: Metalloproteinases: from demolition squad to master regulators. Int J Exp Pathol. 2010;91:303-13.
Murphy, The ADAMs: signalling scissors in the tumour microenvironment. Nat Rev Cancer. Dec. 2008;8(12):929-41. Epub Nov. 13, 2008.
Nath et al., Interaction of metargidin (ADAM-15) with alphavbeta3 and alpha5beta1 integrins on different haemopoietic cells. J Cell Sci. Feb. 1999;112 (Pt 4):579-87.
Pan et al., Kuzbanian controls proteolytic processing of Notch and mediates lateral inhibition during *Drosophila* and vertebrate neurogenesis. Cell. Jul. 25, 1997;90(2):271-80.
Poghosyan et al., Phosphorylation-dependent interactions between ADAM15 cytoplasmic domain and Src family protein-tyrosine kinases. J Biol Chem. Feb. 15, 2002;277(7):4999-5007. Epub Dec. 10, 2001.
Prager et al., Vascular endothelial growth factor (VEGF) induces rapid prourokinase (pro-uPA) activation on the surface of endothelial cells. Blood. Feb. 1, 2004;103(3):955-62. Epub Oct. 2, 2003.
Prager et al., Vascular endothelial growth factor receptor-2-induced initial endothelial cell migration depends on the presence of the urokinase receptor. Circ Res. Jun. 25, 2004;94(12):1562-70. Epub May 6, 2004.
Primo et al., Essential role of PDK1 in regulating endothelial cell migration. J Cell Biol. Mar. 26, 2007;176(7):1035-47. Epub Mar. 19, 2007.
Qi et al., Phosphoinositide 3 kinase is critical for survival, mitogenesis and migration but not for differentiation of endothelial cells. Angiogenesis. 1999;3(4):371-80.
Qiu et al., PIK3CA mutations in head and neck squamous cell carcinoma. Clin Cancer Res. Mar. 1, 2006;12(5):1441-6.
Rahman et al., Adam 15 is a negative regulator of endothelial cell migration induced by VEGF-Firbronectin. Presented at "Fibronectin, Integrins and Related Molecules" Gordon Research Conference. Jan. 30-Feb. 4, 2005. 8 slides.
Rahman et al., Adam 15 is essential for regulated angiogenesis and vegf signalling to akt through proteolytic processing of the

(56) References Cited

OTHER PUBLICATIONS urokinase-type plasminogen activator receptor (upar). British Society for Cardiovascular Research Spring Meeting 2007. Abstract No. 003. 2 pages.
Rahman et al., Novel hepatocyte growth factor (HGF) binding domains on fibronectin and vitronectin coordinate a distinct and amplified Met-integrin induced signalling pathway in endothelial cells. BMC Cell Biol. Feb. 17, 2005;6(1):8.
Ruhrberg et al., Spatially restricted patterning cues provided by heparin-binding VEGF-A control blood vessel branching morphogenesis. Genes Dev.Oct. 15, 2002;16(20):2684-98.
Saal et al., PIK3CA mutations correlate with hormone receptors, node metastasis, and ERBB2, and are mutually exclusive with PTEN loss in human breast carcinoma. Cancer Res. Apr. 1, 2005;65(7):2554-9.
Samuels et al., High frequency of mutations of the PIK3CA gene in human cancers.Science. Apr. 23, 2004;304(5670):554. Epub Mar. 11, 2004.
Samuels et al., Mutant PIK3CA promotes cell growth and invasion of human cancer cells. Cancer Cell. Jun. 2005;7(6):561-73.
Saunders et al., Coregulation of vascular tube stabilization by endothelial cell TIMP-2 and pericyte TIMP-3. J Cell Biol. Oct. 9, 2006;175(1):179-91.
Saunders et al., MMP-1 activation by serine proteases and MMP-10 induces human capillary tubular network collapse and regression in 3D collagen matrices. J Cell Sci. May 15, 2005;118(Pt 10):2325-40. Epub May 3, 2005.
Seals et al., The ADAMs family of metalloproteases: multidomain proteins with multiple functions. Genes Dev. Jan. 1, 2003;17(1):7-30.
Sela-Passwell et al., New opportunities in drug design of metalloproteinase inhibitors: combination between structure-function experimental approaches and systems biology. Expert Opin Drug Discov. May 2011;6(5):527-42. doi: 10.1517/17460441.2011.560936. Epub Apr. 21, 2011.
Stalmans et al., Arteriolar and venular patterning in retinas of mice selectively expressing VEGF isoforms. J Clin Invest. Feb. 2002;109(3):327-36.
Takahashi et al., The 230 kDa mature form of KDR/Flk-1 (VEGF receptor-2) activates the PLC-gamma pathway and partially induces mitotic signals in NIH3T3 fibroblasts. Oncogene. May 1, 1997;14(17):2079-89.
Tape et al., Cross-domain inhibition of TACE ectodomain. Proc Natl Acad Sci U S A. Apr. 5, 2011;108(14):5578-83. doi: 10.1073/pnas.1017067108. Epub Mar. 17, 2011.
Trochon et al., Endothelial metalloprotease-disintegrin protein (ADAM) is implicated in angiogenesis in vitro. Angiogenesis. 1998;2(3):277-85.
Uemura et al., Tlx acts as a proangiogenic switch by regulating extracellular assembly of fibronectin matrices in retinal astrocytes. J Clin Invest. Feb. 2006;116(2):369-77. Epub Jan. 19, 2006.
White, ADAMs: modulators of cell-cell and cell-matrix interactions. Curr Opin Cell Biol. Oct. 2003;15(5):598-606.
Wijelath et al., Fibronectin promotes VEGF-induced CD34 cell differentiation into endothelial cells. J Vasc Surg. Mar. 2004;39(3):655-60.
Wijelath et al., Heparin-II domain of fibronectin is a vascular endothelial growth factor-binding domain: enhancement of VEGF biological activity by a singular growth factor/matrix protein synergism. Circ Res. Oct. 13, 2006;99(8):853-60. Epub Sep. 28, 2006.
Wijelath et al., Novel vascular endothelial growth factor binding domains of fibronectin enhance vascular endothelial growth factor biological activity. Circ Res. Jul. 12, 2002;91(1):25-31.
Yamaoka-Tojo et al., IQGAP1 mediates VE-cadherin-based cell-cell contacts and VEGF signaling at adherence junctions linked to angiogenesis. Arterioscler Thromb Vasc Biol. Sep. 2006;26(9):1991-7. Epub Jun. 8, 2006.
Yang et al., The ADAMs family: coordinators of nervous system development, plasticity and repair. Prog Neurobiol. Jun. 2006;79(2):73-94. Epub Jul. 7, 2006.
Zhang et al., Extracellular matrix regulates endothelial functions through interaction of VEGFR-3 and integrin alpha5beta1. J Cell Physiol. Jan. 2005;202(1):205-14.
Zhang et al., Specific interaction of the recombinant disintegrin-like domain of MDC-15 (metargidin, ADAM-15) with integrin alphavbeta3. J Biol Chem. Mar. 27, 1998;273(13):7345-50.

* cited by examiner

A

B

SEQ ID NO: 1

```
1    mrlallwalg  llgagsplps  wplpniggte  eqqaesekap  replepqvlq  ddlpislkkv
61   lqtslpeplr  ikleldgdsh  ilellqnrel  vpgrptlvwy  qpdgtrvvse  ghtlenccyq
121  grvrgyagsw  vsictcsglr  glvvltpers  ytleqgpgdl  qgppiisriq  dlhlpghtca
181  lswresvhtq  tppehplgqr  hirrrrdvvt  etktvelviv  adhseaqkyr  dfqhllnrtl
241  evallldtff  rplnvrvalv  gleawtqrdl  veispnpavt  lenflhwrra  hllprlphds
301  aqlvtgtsfs  gptvgmaiqn  sicspdfsgg  vnmdhstsil  gvassiahel  ghslgldhdl
361  pgnscpcpgp  apaktcimea  stdflpglnf  sncsrralek  alldgmgscl  ferlpslppm
421  aafcgnmfve  pgeqcdcgfl  ddcvdpccds  ltcqlrpgaq  casdgpccqn  cqlrpsgwqc
481  rptrgdcdlp  efcpgdssqc  ppdvslgdge  pcaggqavcm  hgrcasyaqq  cqslwgpgaq
541  paaplclqta  ntrgnafgsc  grnpsgsyvs  ctprdaicgq  lqcqtgrtqp  llgsirdllw
601  etidvngtel  ncswvhldlg  sdvaqplltl  pgtacgpglv  cidhrcqrvd  llgaqecrsk
661  chghgvcdsn  rhcyceegwa  ppdcttqlka  tsslttglll  sllvllvlvm  lgagywyrar
721  lhqrlcqlkg  ptcqyraaqs  gpserpgppq  rallargtks  qgpakppppr  kplpadpqgr
781  cpsgdlpgpg  agipplvvps  rpappppptvs  slyl
```

Fig. 8

SEQUENCE LISTING

```
<160> NUMBER OF SEQ ID NOS: 8

<210> SEQ ID NO 1
<211> LENGTH: 814
<212> TYPE: PRT
<213> ORGANISM: homo sapiens

<400> SEQUENCE: 1

Met Arg Leu Ala Leu Leu Trp Ala Leu Gly Leu Leu Gly Ala Gly Ser
1               5                   10                  15

Pro Leu Pro Ser Trp Pro Leu Pro Asn Ile Gly Gly Thr Glu Glu Gln
            20                  25                  30

Gln Ala Glu Ser Glu Lys Ala Pro Arg Glu Pro Leu Glu Pro Gln Val
        35                  40                  45

Leu Gln Asp Asp Leu Pro Ile Ser Leu Lys Lys Val Leu Gln Thr Ser
    50                  55                  60

Leu Pro Glu Pro Leu Arg Ile Lys Leu Glu Leu Asp Gly Asp Ser His
65                  70                  75                  80

Ile Leu Glu Leu Leu Gln Asn Arg Glu Leu Val Pro Gly Arg Pro Thr
                85                  90                  95

Leu Val Trp Tyr Gln Pro Asp Gly Thr Arg Val Val Ser Glu Gly His
            100                 105                 110

Thr Leu Glu Asn Cys Cys Tyr Gln Gly Arg Val Arg Gly Tyr Ala Gly
        115                 120                 125

Ser Trp Val Ser Ile Cys Thr Cys Ser Gly Leu Arg Gly Leu Val Val
    130                 135                 140

Leu Thr Pro Glu Arg Ser Tyr Thr Leu Glu Gln Gly Pro Gly Asp Leu
145                 150                 155                 160

Gln Gly Pro Pro Ile Ile Ser Arg Ile Gln Asp Leu His Leu Pro Gly
                165                 170                 175
```

```
His Thr Cys Ala Leu Ser Trp Arg Glu Ser Val His Thr Gln Thr Pro
            180                 185                 190

Pro Glu His Pro Leu Gly Gln Arg His Ile Arg Arg Arg Asp Val
        195                 200                 205

Val Thr Glu Thr Lys Thr Val Glu Leu Val Ile Val Ala Asp His Ser
210                 215                 220

Glu Ala Gln Lys Tyr Arg Asp Phe Gln His Leu Leu Asn Arg Thr Leu
225                 230                 235                 240

Glu Val Ala Leu Leu Leu Asp Thr Phe Phe Arg Pro Leu Asn Val Arg
                245                 250                 255

Val Ala Leu Val Gly Leu Glu Ala Trp Thr Gln Arg Asp Leu Val Glu
                260                 265                 270

Ile Ser Pro Asn Pro Ala Val Thr Leu Glu Asn Phe Leu His Trp Arg
                275                 280                 285

Arg Ala His Leu Leu Pro Arg Leu Pro His Asp Ser Ala Gln Leu Val
        290                 295                 300

Thr Gly Thr Ser Phe Ser Gly Pro Thr Val Gly Met Ala Ile Gln Asn
305                 310                 315                 320

Ser Ile Cys Ser Pro Asp Phe Ser Gly Gly Val Asn Met Asp His Ser
                325                 330                 335

Thr Ser Ile Leu Gly Val Ala Ser Ser Ile Ala His Glu Leu Gly His
                340                 345                 350

Ser Leu Gly Leu Asp His Asp Leu Pro Gly Asn Ser Cys Pro Cys Pro
        355                 360                 365

Gly Pro Ala Pro Ala Lys Thr Cys Ile Met Glu Ala Ser Thr Asp Phe
370                 375                 380

Leu Pro Gly Leu Asn Phe Ser Asn Cys Ser Arg Arg Ala Leu Glu Lys
385                 390                 395                 400

Ala Leu Leu Asp Gly Met Gly Ser Cys Leu Phe Glu Arg Leu Pro Ser
                405                 410                 415

Leu Pro Pro Met Ala Ala Phe Cys Gly Asn Met Phe Val Glu Pro Gly
                420                 425                 430

Glu Gln Cys Asp Cys Gly Phe Leu Asp Asp Cys Val Asp Pro Cys Cys
        435                 440                 445

Asp Ser Leu Thr Cys Gln Leu Arg Pro Gly Ala Gln Cys Ala Ser Asp
450                 455                 460

Gly Pro Cys Cys Gln Asn Cys Gln Leu Arg Pro Ser Gly Trp Gln Cys
465                 470                 475                 480

Arg Pro Thr Arg Gly Asp Cys Asp Leu Pro Glu Phe Cys Pro Gly Asp
                485                 490                 495

Ser Ser Gln Cys Pro Pro Asp Val Ser Leu Gly Asp Gly Glu Pro Cys
        500                 505                 510

Ala Gly Gly Gln Ala Val Cys Met His Gly Arg Cys Ala Ser Tyr Ala
        515                 520                 525

Gln Gln Cys Gln Ser Leu Trp Gly Pro Gly Ala Gln Pro Ala Ala Pro
        530                 535                 540

Leu Cys Leu Gln Thr Ala Asn Thr Arg Gly Asn Ala Phe Gly Ser Cys
545                 550                 555                 560

Gly Arg Asn Pro Ser Gly Ser Tyr Val Ser Cys Thr Pro Arg Asp Ala
                565                 570                 575

Ile Cys Gly Gln Leu Gln Cys Gln Thr Gly Arg Thr Gln Pro Leu Leu
                580                 585                 590
```

-continued

```
Gly Ser Ile Arg Asp Leu Leu Trp Glu Thr Ile Asp Val Asn Gly Thr
            595                 600                 605

Glu Leu Asn Cys Ser Trp Val His Leu Asp Leu Gly Ser Asp Val Ala
        610                 615                 620

Gln Pro Leu Leu Thr Leu Pro Gly Thr Ala Cys Gly Pro Gly Leu Val
625                 630                 635                 640

Cys Ile Asp His Arg Cys Gln Arg Val Asp Leu Leu Gly Ala Gln Glu
                645                 650                 655

Cys Arg Ser Lys Cys His Gly His Gly Val Cys Asp Ser Asn Arg His
            660                 665                 670

Cys Tyr Cys Glu Glu Gly Trp Ala Pro Pro Asp Cys Thr Thr Gln Leu
        675                 680                 685

Lys Ala Thr Ser Ser Leu Thr Thr Gly Leu Leu Leu Ser Leu Leu Val
690                 695                 700

Leu Leu Val Leu Val Met Leu Gly Ala Gly Tyr Trp Tyr Arg Ala Arg
705                 710                 715                 720

Leu His Gln Arg Leu Cys Gln Leu Lys Gly Pro Thr Cys Gln Tyr Arg
                725                 730                 735

Ala Ala Gln Ser Gly Pro Ser Glu Arg Pro Gly Pro Pro Gln Arg Ala
            740                 745                 750

Leu Leu Ala Arg Gly Thr Lys Ser Gln Gly Pro Ala Lys Pro Pro Pro
        755                 760                 765

Pro Arg Lys Pro Leu Pro Ala Asp Pro Gln Gly Arg Cys Pro Ser Gly
770                 775                 780

Asp Leu Pro Gly Pro Gly Ala Gly Ile Pro Pro Leu Val Val Pro Ser
785                 790                 795                 800

Arg Pro Ala Pro Pro Pro Thr Val Ser Ser Leu Tyr Leu
                805                 810

<210> SEQ ID NO 2
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (3)..(4)
<223> OTHER INFORMATION: Xaa = any amino acid
<220> FEATURE:
<221> NAME/KEY: MISC_FEATURE
<222> LOCATION: (6)..(7)
<223> OTHER INFORMATION: Xaa = any amino acid
<220> FEATURE:
<221> NAME/KEY: MISC_FEATURE
<222> LOCATION: (9)..(10)
<223> OTHER INFORMATION: Xaa = any amino acid
<220> FEATURE:
<221> NAME/KEY: MISC_FEATURE
<222> LOCATION: (11)..(11)
<223> OTHER INFORMATION: Xaa = His (H) or Asp (D)

<400> SEQUENCE: 2

His Glu Xaa Xaa His Xaa Xaa Gly Xaa Xaa Xaa
1               5                   10

<210> SEQ ID NO 3
<211> LENGTH: 14
<212> TYPE: PRT
<213> ORGANISM: artificial sequence
<220> FEATURE:
<223> OTHER INFORMATION: synthetic polypeptide
```

-continued

<400> SEQUENCE: 3

Ile Ala His Glu Leu Gly His Ser Leu Gly Leu Asp His Asp
1               5                   10

<210> SEQ ID NO 4
<211> LENGTH: 31
<212> TYPE: DNA
<213> ORGANISM: artificial sequence
<220> FEATURE:
<223> OTHER INFORMATION: synthetic oligonucleotide

<400> SEQUENCE: 4
aactccatct gttctcctga cttcctgtct c                                31

<210> SEQ ID NO 5
<211> LENGTH: 32
<212> TYPE: DNA
<213> ORGANISM: artificial sequence
<220> FEATURE:
<223> OTHER INFORMATION: synthetic oligonucleotide

<400> SEQUENCE: 5
aaaagtcagg agaacagatg gagcctgttc tc                               32

<210> SEQ ID NO 6
<211> LENGTH: 32
<212> TYPE: DNA
<213> ORGANISM: artificial sequence
<220> FEATURE:
<223> OTHER INFORMATION: synthetic oligonucleotide

<400> SEQUENCE: 6
aagcccttcc ttccagttac ctttcctgtc tc                               32

<210> SEQ ID NO 7
<211> LENGTH: 31
<212> TYPE: DNA
<213> ORGANISM: artificial sequence
<220> FEATURE:
<223> OTHER INFORMATION: synthetic oligonucleotide

<400> SEQUENCE: 7
aaaaaggtaa ctggaaggaa ggccctgtct c                                31

<210> SEQ ID NO 8
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(5)
<223> OTHER INFORMATION: N-terminal protecting group, includes Ac and
      1-5 amino acids (Xaa 1-5)
<220> FEATURE:
<221> NAME/KEY: MISC_FEATURE
<222> LOCATION: (20)..(24)
<223> OTHER INFORMATION: C-terminal protecting group, includes NH2 and
      1-5 amino acids (Xaa 20-24)
<220> FEATURE:
<221> NAME/KEY: MISC_FEATURE
<222> LOCATION: (1)..(1)
<223> OTHER INFORMATION: may be missing
<220> FEATURE:
<221> NAME/KEY: MISC_FEATURE
<222> LOCATION: (2)..(2)
<223> OTHER INFORMATION: may be missing
<220> FEATURE:

```
<221> NAME/KEY: MISC_FEATURE
<222> LOCATION: (3)..(3)
<223> OTHER INFORMATION: may be missing
<220> FEATURE:
<221> NAME/KEY: MISC_FEATURE
<222> LOCATION: (4)..(4)
<223> OTHER INFORMATION: may be missing
<220> FEATURE:
<221> NAME/KEY: MISC_FEATURE
<222> LOCATION: (21)..(21)
<223> OTHER INFORMATION: may be missing
<220> FEATURE:
<221> NAME/KEY: MISC_FEATURE
<222> LOCATION: (22)..(22)
<223> OTHER INFORMATION: may be missing
<220> FEATURE:
<221> NAME/KEY: MISC_FEATURE
<222> LOCATION: (23)..(23)
<223> OTHER INFORMATION: may be missing
<220> FEATURE:
<221> NAME/KEY: MISC_FEATURE
<222> LOCATION: (24)..(24)
<223> OTHER INFORMATION: may be missing

<400> SEQUENCE: 8

Xaa Xaa Xaa Xaa Xaa Ile Ala His Glu Leu Gly His Ser Leu Gly Leu
1               5                   10                  15

Asp His Asp Xaa Xaa Xaa Xaa Xaa
            20
```

ADAM-15 ANTIBODIES AND IMMUNOGENIC PEPTIDES

RELATED APPLICATIONS

This application claims priority to U.S. provisional application No. 61/038,837, filed Mar. 24, 2008, the content of which is incorporated herein by reference in its entirety.

FIELD OF THE INVENTION

Aspects of the present invention relate to antibodies and antigen-binding fragments thereof, and immunogenic peptides, methods and uses thereof, and kits comprising said antibodies, fragments and peptides.

BACKGROUND OF THE INVENTION

Cancer is one of the world's biggest killers, with estimates that 7.6 million people died of cancer in 2005—representing 13% of deaths worldwide. Between 2005 and 2015, 84 million more people will die if urgent action is not taken (WHO forecast). Such statistics have prompted a largescale investment in cancer research in both the public health and private sectors. Therefore, there is an urgent need to translate medical research towards the development of novel cancer treatments and drugs.

It was Folkman's group in the early 70's that performed definitive experiments demonstrating the release by implanted tumours of soluble factors that promote the induction of angiogenesis within the host leading to the recruitment of a blood supply supporting tumour growth and metastasis. These pioneering experiments suggested that abrogation of tumour angiogenesis would be a viable anti-cancer therapeutic strategy and this has been supported by pre-clinical studies. The development of anti-angiogenic drugs including monoclonal antibodies (Avastin) to the important angiogenic factor VEGF has led to the successful application of this strategy in the clinic. Anti-angiogenic drugs in combination with standard chemotherapy have generated impressive results in clinical trials. However, drugs such as Avastin have shown signs of promoting severe side effects and this has prompted the search for more selective and milder alternatives.

Angiogenesis is the process of neocapillary sprouting from pre-existing vessels in response to signals induced by hypoxia. Physiological angiogenesis is a finely regulated process involving the interplay between distinct vascular cell types incorporating a host of humoural regulatory molecules controlling and coordinating primarily endothelial and smooth muscle cell responses. Newly developing vessels are organised into a patterned vascular network that is directed by the hypoxic requirements of a particular organ but, nonetheless, undergo common cell-coordinated responses such as migration, proliferation, tubulogenesis, and remodelling.

The most important physiological humoural mediator of angiogenesis is VEGF-A which controls vessel permeability, endothelial cell (EC) proliferation and survival, migration and morphogenetic processes associated with vascular patterning (1). The challenge to understanding the biology of angiogenesis is the elucidation of the spatiotemporal regulation of VEGF A signalling that controls the sequential processes during capillary sprouting, growth and maturation.

Recent work has highlighted the important role of the specialisation of the endothelial compartment of sprouting vessels. Gerhardt et al showed in the retina that specialized tip cells characterised by extensive filopodia present at the migrating front of the developing vascular plexus guide vascular patterning in response to matrix associated gradients of VEGF A. In contrast, cells comprising the vessel stalk proliferate in response to soluble VEGF A concentration (2, 3). At the molecular level, we and others have shown that the extracellular matrix (ECM) component fibronectin (Fn) augments EC responses induced by VEGF A through collaborative signalling between the receptor tyrosine kinase VEGFR2 and the integrin $\alpha_5\beta_1$ (4-6). We identified and mapped a VEGF binding domain within domains $III_{12-14}$ of the Hep II region of Fn that augments VEGF A/VEGFR2 mediated EC responses (7). The combined activity of the Hep II VEGF binding domain and the cell-binding domain encompassing modules $III_9$-$III_{10}$ present within a single Fn fragment was indispensable for signal amplification.

While the discovery of binding domains in Fn and further VEGF A sequestration by additional ECM components such as heparan sulphate proteoglycans (2) provide molecular insights into how matrix-associated VEGF A gradients are established to drive tip cell migration, the VEGF A-dependent mechanisms that regulate capillary stalk morphogenesis and integrity are not well understood. Evidence highlighting the necessity of controlling VEGF concentration during vasculogenesis have come from studies employing VEGFR1 null mice which showed that embryonic lethality is caused by abnormal vessel development in utero characterised by vascular overgrowth, a consequence of dysregulated endothelial cell proliferation (8). Furthermore, during development, the extracellular domain of VEGFR1 was sufficient to support vasculogenesis in VEGFR1 kinase null mice supporting the notion that controlling VEGF A concentration is an important physiological parameter in regulating angiogenesis through controlling the proliferative capacity of endothelial cells (9).

These studies illustrate that during angiogenesis/vasculogenesis signalling through the VEGF A-VEGFR2 axis is regulated through multiple pathways utilising several distinct families of receptors, specially adapted endothelial subpopulations and the spatial regulation of VEGF concentration and gradients established in association with components of the ECM. This raises the possibility that additional molecules may also be involved in regulating VEGFR2 dependent processes including those regulating stalk cell behaviour. A potential candidate gene family for the regulation of VEGF signalling and angiogenesis are the ADAMs family of disintegrin-metalloproteases that have been implicated in modulating many cellular processes including adhesion, fusion, differentiation and surface protein shedding (10). ADAM's proteins were initially identified as important regulators of gamete fusion but have since been implicated in several other physiological processes including neurogenesis, myogenesis and the regulation of the inflammatory response (11, 12). The presence of a disintegrin domain has been shown to mediate integrin binding, although the physiological consequence of this activity in many ADAMs family members remains controversial. However, the biological function of their metalloprotease activity shows increasing prominence in the process of protein ectodomain shedding. For example, ADAM 17 or TACE has been shown to proteolytically process the precursor form of the pro-inflammatory cytokine TNFα, thereby promoting the release of the active cytokine from the cell surface (13). In addition, mammalian ADAM 10 (MADM) was also shown to possess TNFα-converting activity whereas the *Drosophila* ortholog KUZ is known to regulate notch signalling through cleavage of its extracellular domain promoting lateral inhibition during neurogenesis (14, 15) Furthermore, ADAM 13 which is expressed in *Xenopus* neural crest cells, is necessary for their migratory activity required for later stages of neurogenesis and this is thought to be due to the re-modelling (cleavage) of Fn by the metalloprotease domain (16, 17). Lastly, ADAM 17 has been reported to be responsible for the ectodomain shedding of GP1bα and GP V, components of the receptor complex for vWF, from platelets after treatment with aspirin (18). Therefore, it is conceivable that members of the ADAMs family could regulate VEGF A mediated responses through mechanisms involving these established biological activities or via hitherto unappreciated modes of action.

Previous studies have shown that ADAM 15 is expressed in cultured EC and smooth muscle cells (SMC) and its expression is elevated in diseased vascular tissue (19) suggesting a role in pathological vascular remodelling. ADAM 15 is a family member with a predicted active metalloprotease which is expressed in cells of haematopoeitic and neural origin. The human orthologue of ADAM 15, metargidin, is the only ADAM family member with an active canonical RGD sequence within its disintegrin domain (20). ADAM 15 has also been co-localised to the adherens junctions of endothelium with VE-cadherin suggesting that ADAM 15 may be involved in processes involving these cell junctions (21).

In 2003, it was shown that ADAM $15^{-/-}$ null mice develop normally but exhibit impaired pathological angiogenesis. This lead to speculation about a potential role for ADAM 15 in pathological neovasculization in mice (22).

In 2004, Blobel et al. (51) suggested that therapeutic agents which inhibit ADAM 9 and/or ADAM 15 might be used for the treatment of vascularization-related disease or wound healing. Antibodies, small molecule therapeutics, antisense RNAs and an agent for introducing targeted mutations in the genetic sequence of ADAM 9 or ADAM 15 were suggested in this regard although not exemplified. Suitable targets for the development of antibody therapies were said to include intact ADAM9, intact ADAM15, portions of ADAM9 or ADAM15 derived from the extracellular portions of the protein; the protease and disintegrin domains of the extracellular portions were also postulated as potential targets. However, no data in support of the action of such therapeutic agents was presented and no antibodies were exemplified.

In 2005, Rahman et al. (52) disclosed two polyclonal rabbit sera (Ab 576 and Ab 577) against a peptide corresponding to amino acid residues 346-359 of the human ADAM 15 polypeptide. (Amino acid residues 346-359 fall within the metalloprotease domain of ADAM 15 proximal to the predicted catalytic cleft). Affinity-purified antibodies derived from these sera were used to investigate the effect that ADAM 15 has on endothelial cell migration in a Boyden chamber assay. In direct contrast to the suggestions put forward in Blobel (51), these anti-metalloprotease domain directed antibodies were found to promote a 2-3 fold elevation in endothelial cell migration (FIG. 5) of Rahman et al. This effect was confirmed by gene silencing (siRNA to ADAM 15) experiments. These experiments appeared to show that antibodies against the metalloprotease domain of ADAM 15 could therefore potentially promote vascularization and hence such antibodies would not be suitable as agents for the prevention of neovascularization or angiogenesis.

SUMMARY OF THE INVENTION

Aspects of the present invention relate to antibodies and antigen-binding fragments thereof, which, in certain embodiments are capable of inhibiting neovascularization and/or angiogenesis. Aspects of the present invention also relate to peptide(s) that, in certain embodiments, comprise the principal/active component of a vaccine preventing neovascularisation and/or angiogenesis. In certain embodiments, the invention relates to antibodies and antigen-binding fragments thereof with neutralizing specificity towards the metalloprotease domain of ADAM 15. In certain embodiments, the invention relates to an immunogenic peptide region(s) of the metalloprotease domain of ADAM 15 that elicits antibodies targeting ADAM 15 function. In certain embodiments, the invention relates to compositions and kits comprising the antibodies and peptides of described herein, as well as methods and uses of the antibodies and antigen-binding fragments thereof, and immunogenic peptides.

The inventors have now found that, whilst anti-ADAM 15 antibodies are capable of promoting endothelial cell migration in vitro, ADAM 15, itself, promotes endothelial cell proliferation. Aspects of the invention are based at least in part on the unexpected finding that antibodies against ADAM 15 are capable of impairing angiogenesis in vivo by blocking endothelial cell proliferation and survival (FIGS. 2 and 3). A similar result has been obtained using siRNA specific for ADAM 15 in vitro.

Without wanting to be bound by any particular theory, the inhibitory effect of anti-ADAM-15 antibodies and/or siRNA upon cell proliferation appears to be associated with the activation state of the Akt kinase (Protein Kinase B), a downstream effector of the enzyme PI3 kinase (FIG. 4). The PI3 kinase-Akt pathway is thought to be particularly important in the pathogenesis of several cancers as somatic mutations in the genes of the enzymes of this pathway that lead to enhanced activity have been reported in tumour isolates of several cancers (53-60). In certain embodiments, anti-ADAM 15 antibodies are able to inhibit activation of the Akt kinase.

The finding that, in certain embodiments, anti-ADAM 15 antibodies have an inhibitory effect on angiogenesis is particularly surprising given the previous teachings in the art towards the promotion of endothelial cell migration by anti-ADAM 15 antibodies (52). Aspects of the invention also relate to the finding that ADAM 15, in certain embodiments, targets the urokinase receptor uPAR for proteolysis in endothelial cells and in the mononuclear cell line U937 (FIG. 6), indicating that ADAM 15 may serve as a physiological negative regulator of plasminogen activation, the end point of an important proteolytic system regulating several physiological and pathophysiological processes including those associated with inflammation (61). Plasmin is a serine protease responsible for the degradation of fibrin and other extracellular matrix components that assemble as a consequence of damaged or leaky blood vessels (61). Plasmin also activates matrix metalloproteases that degrade the extracellular matrix leading to the disruption of immobilised growth factor/cytokine gradients important for directed cell movement and tissue patterning (2, 3, 62). Without wanting to be bound by a particular theory, the reported elevation of ADAM 15 in both inflammatory cells in conditions such as rheumatoid arthritis or inflammatory bowel disease (63) and in metastasizing cancers (64) may also reflect a role in regulating extracellular plasmin formation through the controlled degradation of uPAR, in a manner that supports immune cell infiltration or tumour cell invasion/metastasis. In certain embodiments, anti-ADAM 15 antibodies may inhibit uPAR degradation and may increase pericellular plasmin generation and may disrupt immune cell infiltration and cancer cell metastasis through a dysregulation of pericellular proteolytic environment.

Certain aspects of the invention, provide antibodies which can be used to prevent neovascularization and which can be used to prevent angiogenesis, particularly in tumours, and to treat and non-tumour pathologies including proliferative retinopathies and inflammatory/proliferative vascular disorders such atherosclerosis and restenosis, respectively. The invention, in certain aspects, also provides an immunogenic peptide region derived from the metalloprotease domain of ADAM 15 that may elicit, in certain embodiments, the production of function-blocking antibodies against ADAM 15, despite cross-species conservation of this sequence.

One advantage of some aspects of the present invention is that, in some embodiments, the antibodies described herein target a polypeptide (ADAM 15), which may not be required for normal development or for adult homeostasis.

In a first aspect, the invention provides an isolated antibody or antigen-binding fragment thereof which specifically recognizes human ADAM 15 polypeptide, wherein the antibody is a non rabbit-polyclonal antibody, and wherein the antibody or antigen-binding fragment is capable of inhibiting proliferation of endothelial cells.

In some embodiments of the invention, the antibody or antigen-binding fragment is capable of inhibiting proliferation of a population of endothelial cells when the antibody or antigen-binding fragment is applied to said population.

In certain embodiments, the endothelial cells may be human dermal microvessel endothelial cells (HMVECs) which have been maintained, for example, in EBM-2 growth medium. Proliferation may be tested using a standard cell division assay, for example as described in Example 1.

In a further aspect, the invention provides an isolated antibody or antigen-binding fragment thereof which specifically recognizes human ADAM 15 polypeptide, wherein the antibody is a non rabbit-polyclonal antibody, and wherein the antibody or antigen-binding fragment is capable of inhibiting angiogenesis.

In some embodiments, the invention also provides an isolated antibody or antigen-binding fragment thereof which specifically recognizes human ADAM 15 polypeptide, wherein the antibody is a non rabbit-polyclonal antibody, and wherein the antibody is capable of preventing proteolytic cleavage of the urokinase receptor uPAR by ADAM 15.

In a further aspect, the invention provides an isolated antibody or antigen-binding fragment thereof which specifically recognizes the metalloprotease domain of the human ADAM 15 polypeptide, wherein the antibody is a non rabbit-polyclonal antibody.

In some embodiments, the antibody is a non-rabbit antibody. In other embodiments, the antibody is a non-polyclonal antibody.

In some aspects, the antibody or antigen binding fragment specifically recognizes the proteolytic cleft of the metalloprotease domain.

In some aspects, the human ADAM 15 polypeptide is a polypeptide of SEQ ID NO: 1. It will be appreciated by the person skilled in the art, however, that natural variations of this sequence exist in the human population and that SEQ ID NO: 1 is given merely as an example of one such sequence. It should be appreciated that the invention is not limited to a human ADAM 15 polypeptide sequence of SEQ ID NO: 1.

BRIEF DESCRIPTION OF THE FIGURES

FIG. 8. shows the human ADAM 15 amino acid precursor sequence (AAC50404).

BRIEF DESCRIPTION OF THE SEQUENCES

Figure 1:
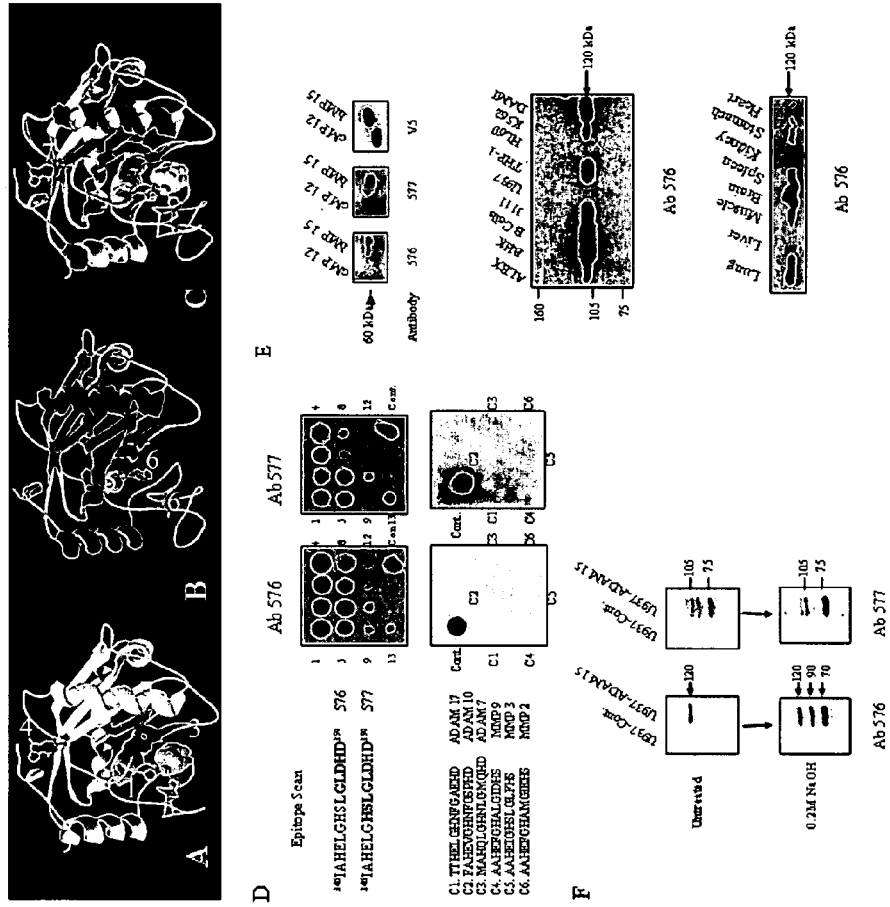
FIG. 1. illustrates non-limiting embodiments of the development and characterisation of ADAM 15 MP domain site-specific antibodies.

SEQ ID NO: 1 shows the amino acid sequence of the human form of ADAM 15.

SEQ ID NO: 2 shows the amino acid consensus sequence of the ADAM 15 metalloprotease domain.

SEQ ID NO: 3 shows the amino acid sequence of amino acids 346-359 of the human form of ADAM 15.

SEQ ID NOs: 4-7 are ADAM 15 specific primers.

SEQ ID NO: 8 corresponds to SEQ ID NO: 3 with additional N- and/or C-terminal protecting groups.

DETAILED DESCRIPTION

Aspects of the invention relate to inhibitors of ADAM 15 and their use for therapeutic applications. Aspects of the invention are based, at least in part, on the involvement of ADAM 15 in neovascularization and/or angiogenesis. In some embodiments, inhibition of the protease activity of ADAM 15 can be useful to reduce or prevent neovascularization and/or angiogenesis in subjects having a disease or disorder associated with neovascularization and/or angiogenesis. In some embodiments, inhibition of the protease activity of ADAM 15 can be useful to treat a condition or disorder associated with inflammation. In some embodiments, inhibition of the protease activity of ADAM 15 can be useful to treat a condition or disorder such as acute macular degeneration or retinopathy.

The term "antibody" as used herein refers to immunoglobulin molecules or other molecules which comprise at least one antigen-binding domain.

The term "antibody" as used herein is intended to include whole antibodies (e.g. IgG, IgA, IgE, IgM, or IgD), monoclonal antibodies, polyclonal antibodies, humanized, chimeric antibodies, human antibodies and totally synthetic and recombinant antibodies.

Polyclonal antibodies can be produced in vivo in response to immunization with different epitopes on an immunogen. Anti-serum may be raised in a wide range of animals with one or more injections of an antigen optionally along with a non-specific enhancer of the immune response, such as an adjuvant. For many small molecules or haptens, a carrier protein, which may provide determinants recognized by helper T-cells, may be required for conjugation via various bi-functional coupling reagents. Upon one or more immunizations, the antibodies produced may be predominantly IgG with some affinity to the epitope. Polyclonal antibodies provide multiple specificity. The specificity of polyclonal antibodies may be improved by affinity chromatography using purified antigen.

Monoclonal antibodies may be produced in animals such as mice and rats by immunization. B cells can be isolated from the immunized animal, for example from the spleen. The isolated B cells can be fused, for example with a myeloma cell line, to produce hybridomas, that can be maintained indefinitely in in vitro cultures. These hybridomas can be isolated by dilution (single cell cloning) and grown into colonies.

Individual colonies can be screened for the production of antibodies of uniform affinity and specificity. Hybridoma cells may be grown in tissue culture and antibodies may be isolated from the culture medium. Hybridoma cells may also be injected into an animal, such as a mouse, to form tumors in vivo (such as peritoneal tumors) that produce antibodies that can be harvested as intraperitoneal fluid (ascites). The lytic complement activity of serum may be optionally inactivated, for example by heating.

Proteins, peptides, haptens, chemical compounds, may be used to generate antibodies. Peptides, haptens, and small compounds may, in some embodiments, be conjugated to a carrier protein to elicit an immune response. Antibody titers can be monitored by antigen-specific ELISA. One or more animals are commonly used for antibody production, such as rabbits, sheep, goats, chicken, mice, rats, hamsters, and guinea pigs.

After one or more injections of the antigen, approximately 7-10 days after each boost, serum may be taken to determine the production of specific antibodies (titer). The test bleeds may be assayed against the immunogen itself, for example in an ELISA assay.

Antibodies may be stored in several different buffers, for example at neutral pH, such as 0.01M phosphate-buffered saline (PBS) at pH 7.4, optionally containing, for example 0.1% sodium azide to inhibit microbial growth. For long-term storage, antibodies may be kept at a low temperature, such as 4° C., −20° C. or −70° C. Antibodies may be stored at >0.5 mg/mL and/or in the presence of a carrier protein (e.g., 1% bovine serum albumin (BSA)), or if frozen, for example in 50% glycerol.

Protocols for generating antibodies, including preparing immunogens, immunization of animals, and collection of antiserum may be found in *Antibodies: A Laboratory Manual*, E. Harlow and D. Lane, ed., Cold Spring Harbor Laboratory (Cold Spring Harbor, N.Y., 1988) pp. 55-120.

The term "antibody fragment" as used herein is intended to include any appropriate antibody fragment which comprises an antigen-binding domain that displays antigen binding function. Examples of antibody fragments include Fab, Fab', F(ab')$_2$, scFv, Fv, dsFv, ds-scFv, Fd, dAbs, T and Abs dimers, minibodies, diabodies, and multimers thereof and bispecific antibody fragments.

As used herein, the term "non rabbit-polyclonal antibody" means that the antibody is not a rabbit polyclonal antibody.

Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, Fv, dsFv, Fd, dAbs, T and Abs, ds-scFv, dimers, minibodies, diabodies, bispecific antibody fragments and other fragments can also be synthesized by recombinant techniques or can be chemically synthesized. Techniques for producing antibody fragments are well known and described in the art.

In some aspects, the antibody or antibody fragment comprises an antibody light chain variable region (VL) and an antibody heavy chain variable region (VH) which generally comprise the antigen binding site. In certain embodiments, the antibody or antibody fragment comprises all or a portion of a heavy chain constant region, such as an IgG1, IgG2, IgG3, IgG4, IgA1, IgA2, IgE, IgM or IgD constant region. In some aspects, the heavy chain constant region is an IgG1 heavy chain constant region, or a portion thereof. Furthermore, the antibody or antibody fragment may comprise all or a portion of a kappa light chain constant region or a lambda light chain constant region, or a portion thereof. In some aspects, the light chain constant region is a lambda light chain constant region, or a portion thereof. All or part of such constant regions may be produced naturally or may be wholly or partially synthetic. Appropriate sequences for such constant regions are well known and documented in the art.

In some embodiments of the invention, the antibodies or antigen-binding fragments thereof are mammalian antibodies or antigen-binding fragments, such as mouse, rat, rabbit, or human antibodies or antigen-binding fragments.

In a certain embodiments, antibodies of the invention are human antibodies. The term "human" as used herein in connection with antibody molecules and fragments thereof refers to antibodies having variable (e.g. VH, VL, CDR or FR regions) and/or constant antibody regions derived from or corresponding to sequences found in humans, e.g. in the human germline or somatic cells.

In some embodiments, human antibodies may be used in human therapy. In such antibodies, the effector portion is human and hence it may interact better with the other parts of the human immune system. They are not recognized by the body as foreign; and they will have half-lives similar to naturally-occurring human antibodies.

In certain embodiments, human antibodies of the invention may also comprise one or more amino acid residues which are not naturally encoded by wild-type human nucleic acid sequences, but which have been artificially changed/introduced in order to modify the sequence of the antibody. For example, 1-5 amino acids might be changed in the antigen binding domain in order to modify (e.g. enhance) the affinity of the original antibody for the ADAM 15 polypeptide.

The ADAM family of disintegrin/metalloproteases are well known in the art (10, 11). As used herein, the term "human ADAM 15" refers to the ADAM 15 polypeptide as isolatable from human tissues. Human ADAM 15 is also known as metargidin. One exemplary sequence of the human ADAM 15 polypeptide is given herein as SEQ ID NO: 1 (FIG. 8); natural human variants of this sequence will be known. The skilled person will appreciate that this sequence is included merely for reference and that the scope of the invention is not to be deemed as being limited to antibodies against polypeptides having this sequence alone.

Other isoforms of ADAM 15 have been deposited. See for example:
gi|46909600|ref|NP_997080.1|[46909600],
gi|46909598|ref|NP_997079.1|[46909598],
gi|46909596|ref|NP_997078.1|[46909596],
gi|46909594|ref|NP_997077.1|[46909594],
gi|46909592|ref|NP_997074.1|[46909592],
gi|46909590|ref|NP_003806.3|[46909590]and
gi|1235674|gb|AAC50404.1|[1235674]

At least 13 human isoforms of ADAM 15 have been reported and different isoforms may be expressed in different cancers. The known human isoforms differ in sequence only within the intracellular portion of the molecule and are differentially spliced. No human isoforms of ADAM 15 have been reported that differ in the extracellular portion of the molecule or that differ within the metalloprotease domain. However, it should be appreciated that aspects of the invention are not limited to characterized isoforms of ADAM 15. Any ADAM 15 isoform or variant may be i) used to generate antibodies (for example based on the metalloprotease domain), and/or ii) targeted therapeutically as described herein.

As used herein, the term "metalloprotease domain" is the region of the ADAM 15 polypeptide which is responsible for the metalloprotease activity of the polypeptide. The metalloprotease domain of ADAM 15 is predicted to conform to the general structure of the metzincin superfamily of metalloendopeptidases. The ADAM 15 metalloprotease domain is thus characterized by a C-terminally elongated motif, HEXXHXXGXXH/D (SEQ ID NO: 2), with an additional strictly conserved glycine and a third zinc-binding histidine or aspartate. This includes a substrate-binding crevice, which subdivides the enzyme moiety into an upper and a lower subdomain. A common five-stranded β-sheet and two α-helices are always found in the upper subdomain. The second of these helices encompasses the first half of the elongated consensus sequence and is therefore termed the active-site helix. Other shared characteristics are an invariant methionine-containing Met-turn beneath the catalytic metal and a further C-terminal helix in the lower subdomain. In some embodiments, the metalloprotease domain is a domain comprising or consisting of the peptide sequence IAHELGHSLGLDHD (SEQ ID NO: 3), or a peptide sequence which has at least 70%, 80%, 90% or 95% sequence identify with SEQ ID NO: 3.

In other embodiments, the antibodies of the invention or as defined herein bind to the proteolytic cleft of the metalloprotease domain.

In the human ADAM 15 amino acid sequence as given herein (SEQ ID NO: 1), the metalloprotease domain comprises amino acids 346-359.

In a further embodiment, the invention provides an isolated antibody or antigen-binding fragment thereof which specifically binds to a peptide comprising or consisting of the amino acid sequence IAHELGHSLGLDHD (SEQ ID NO: 3) or a peptide with at least 70%, at least 80% or at least 90%, sequence identity to SEQ ID NO: 3, wherein the antibody is a non rabbit-polyclonal antibody.

In some embodiments, the antibody is a non-rabbit antibody. In other embodiments, the antibody is a non-polyclonal antibody. In certain embodiments, the antibody is a mouse, humanised, human, recombinant or synthetic antibody.

In a yet further embodiment, the invention provides an isolated antibody or antigen-binding fragment thereof which specifically binds to an epitope on human ADAM 15 polypeptide defined by amino acids 346-359 of SEQ ID NO: 1, wherein the antibody is a non rabbit-polyclonal antibody.

In some embodiments, the antibody is a non-rabbit antibody. In other embodiments, the antibody is a non-polyclonal antibody. In certain embodiments, the antibody is a mouse, humanised, human, recombinant or synthetic antibody.

In certain embodiments, the invention also provides an isolated antibody or antigen-binding fragment thereof which specifically binds to human ADAM 15 polypeptide, wherein the antibody is a non rabbit-polyclonal antibody, and wherein the antibody or antigen-binding fragment thereof binds to the ADAM 15 epitope defined by amino acids 346-359 of SEQ ID NO: 1 such that the antibody prevents proteolytic cleavage of the urokinase receptor uPAR by ADAM 15.

The proteolysis of uPAR by ADAM 15 may be tested in an assay wherein ADAM 15 and uPAR are co-expressed in a suitable cell line, e.g. U937 cells as in Example 7.

In a yet further embodiment, the invention provides an isolated antibody or antigen-binding fragment thereof which specifically binds to an epitope on human ADAM 15 polypeptide defined by the topographic region $His^{352}$, $Ser^{353}$, $Leu^{354}$, $Gly^{355}$, $Leu^{356}$, $Asp^{357}$ and $Asp^{359}$, wherein the antibody is non rabbit-polyclonal antibody.

An isolated antibody or antigen-binding fragment thereof which specifically binds to an epitope on human ADAM 15 polypeptide defined by the topographic region $Leu^{354}$, $Gly^{355}$, $Leu^{356}$, $Asp^{357}$, $His^{358}$ and $Asp^{359}$ wherein the antibody is a non rabbit-polyclonal antibody.

The amino acid numbering referred to above is derived from the human ADAM 15 amino acid sequence as given in SEQ ID NO: 1. The skilled person will appreciate, however, that this numbering is not limiting on this aspect of the invention.

In some embodiments, the antibodies and antigen binding fragments of the invention have one or more of the following properties:
(i) they specifically recognize the metalloprotease domain of the human ADAM 15 polypeptide; and/or optionally the antibody or antigen binding fragment specifically recognizes the proteolytic cleft of the metalloprotease domain;
(ii) they reduce or block, in some embodiments, to a significant level, angiogenesis in vivo;
(iii) they stimulate, in some embodiments, to a significant level, endothelial cell migration in vitro;
(iv) they reduce or inhibit, in some embodiments, to a significant level, endothelial cell proliferation,
(v) they reduce or inhibit VEGF-induced endothelial cell proliferation;
(vi) they do not inhibit VEGF-induced Erk1/2 phosphorylation in endothelial cells;
(vii) they reduce or inhibit VEGF-induced Akt activation in endothelial cells;
(viii) they reduce or inhibit phosphorylation of GSK 3β in endothelial cells;
(ix) they are capable of enhancing plasminogen activation.

In some embodiments, "block," "stimulate," "reduce or inhibit" and "do not inhibit" may be to a level or extend that is significant. In the present context, the term "significant" means that it is statistically significant when compared to a parallel cell population treated with a non-immune IgG control reagent, for example, $p<0.05$, standard t-test.

In some embodiments, "block," "stimulate," "reduce or inhibit" and "do not inhibit" may be a reduction or increase of 0%, 10%, 20%, 30%, 40%, 50%, 60%, 70%, 80%, 90%, 95%, 96%, 97%, 98%, 99%, or 100% when compared to a parallel cell population treated with a non-immune IgG control reagent.

As used herein, the term "specifically recognizes" refers to the fact that the antibody and/or antigen-binding fragment thereof is specific or substantially specific for the human ADAM 15 metalloprotease domain. In other words, the antibodies and antigen-binding fragments thereof do not significantly bind to other polypeptides, and/or they do not bind other polypeptides to an extent which affects the use of the antibodies/fragments in therapeutic or diagnostic applications. In some embodiments, the term "specifically recognizes" means that the antibody binds to the human ADAM 15 metalloprotease domain but not to the ADAM 15 prodomain or disintegrin domain. In some other embodiments, the term "specifically recognizes" means that the antibody binds to the human ADAM 15 metalloprotease domain but does not significantly bind to the metalloprotease domains of one or more of ADAM 12, ADAM 17, ADAM 10, ADAM 7, MMP 2, MMP 3 or MMP 9. In particular, the term "specifically recognizes" also means that the antibody binds to an epitope which comprises 1, 2, 3, 4, 5, 6, 7, 8, 9, 10 or more of the amino acids which comprise the metalloprotease domain.

Methods of determining the binding specificity of antibodies and fragments thereof are well known in the art and include functional, competition assays, ELISA, co-precipitation and cross-reactivity assays including dot blotting, western blotting and radioimmunoassays.

In certain embodiments, the antibodies described herein have a binding affinity for ADAM 15 which corresponds to a Km of less than 1 µM, of less than 500, 400 or 300 nM, of less than 200, 190, 180, 170, 160, 150, 140, 130, 120, 110, or 100 nM, or of less than 90, 80, 70, 60, 50, 40, 30, 20, 10, 5 or 1 nM. For example, the binding affinity may be $1\times10^{-7}$ M or less, or $1\times10^{-8}$ M or less. Any appropriate method of determining Km may be used. The Km may, for example, be determined by testing various concentrations of the antibody against a fixed number of target cells in vitro to establish a saturation curve, for example using the Lineweaver-Burk method.

Aspects of the invention also relate to peptides and polypeptides which are substantially homologous to the antibodies and antigen-binding fragments thereof described herein.

In certain aspects, substantially homologous sequences of antibodies of the invention include, without limitation, those having conservative amino acid substitutions, or for example alterations which do not affect the VH, VL or CDR domains of the antibodies, e.g. include scFv antibodies where a different linker sequence is used or antibodies where tag sequences or other components are added which do not contribute to the binding of antigen, or alterations to convert one type or format of antibody molecule or fragment to another type or format of antibody molecule or fragment (e.g. conversion from Fab to scFv or vice versa), or the conversion of an antibody molecule to a particular class or subclass of antibody molecule (e.g. the conversion of an antibody molecule to IgG or a subclass thereof, e.g. IgG1 or IgG3).

A "conservative amino acid substitution", as used herein, is one in which the amino acid residue is replaced with another amino acid residue having a similar side chain. Families of amino acid residues having similar side chains have been defined in the art, including basic side chains (e.g., lysine, arginine, histidine), acidic side chains (e.g. aspartic acid, glutamic acid), uncharged polar side chains (e.g. glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In certain embodiments, the antibodies and antigen-binding fragments of the invention may also be used to produce further antibodies/fragments which are specific for ADAM 15. Such uses involve for example the addition, deletion, substitution or insertion of one or more amino acids in the amino acid sequence of a parent antibody/fragment to form a new antibody/fragment, wherein said parent antibody is one of the antibodies/fragments of the invention as defined elsewhere herein, and testing the resulting new antibody/fragment to identify antibodies/fragments specific for ADAM 15. Such methods can be used to form multiple new antibodies/fragments which can all be tested for their ability to bind ADAM 15. In certain embodiments, said addition, deletion, substitution or insertion of one or more amino acids takes place in one or more of the CDR domains.

A further aspect of the invention relates to a nucleic acid molecule which encodes an antibody of the invention or an antigen-binding fragment thereof.

In certain embodiments, the invention also provides a nucleic acid molecule which encodes a polypeptide which is substantially homologous to the amino acid sequence of an antibody of the invention or an antigen-binding fragment thereof.

The nucleic acid molecules may be double stranded or single stranded. The nucleic acid molecules may be wholly or partially synthetic or recombinant.

In this context, the term "substantially homologous" means that the polypeptide or peptide has, in certain embodiments, at least 70%, 80%, 90%, 95% or 99% sequence identity to the antibody of the invention or an antigen-binding fragment thereof. Sequence comparisons may be performed either by manual evaluation of the sequence by one skilled in the art, or by computer-automated sequence comparison and identification using algorithms such as BLAST (Basic Local Alignment Search Tool; Altschul, S. F., et al., (1993) J. Mol. Biol. 215:403-410; see also www.ncbi.nlm.nih.gov/BLAST/), the Megalign program of the LASERGENE bioinformatics computing suite (DNASTAR Inc., Madison, Wis.) or using the Clustal method of alignment (Higgins and Sharp (1989) CABIOS. 5: 151-153). If using the Clustal method, default parameters for pairwise alignments may be KTUPLE 1, GAP PENALTY=3, WINDOW=5 and DIAGONALS SAVED=5.

In certain embodiments, the antibodies, antigen-binding fragments and nucleic acid molecules of the invention are g isolated molecules insofar as they are not present in situ within a human or animal body or a tissue sample derived from a human or animal body. Their sequences may, however, correspond to or be substantially homologous to sequences as found in a human or animal body. Thus, the term "isolated" as used herein in reference to nucleic acid molecules or proteins or polypeptides, refers to such molecules when isolated from or substantially free of their natural environment, e.g. isolated from the human or animal body (if indeed they occur naturally), or refers to such molecules when produced by a technical process, for example includes recombinant and synthetically produced molecules. An isolated nucleic acid molecule may also be substantially free of sequences which naturally flank the nucleic acid molecule (e.g. sequences located at the 5' and 3' ends of the nucleic acid) from which the nucleic acid molecule is derived or sequences which have been made to flank the nucleic acid (e.g. tag sequences or other sequence which have no therapeutic value) by for example genetic engineering.

The antibodies or antibody fragments can be produced naturally or can be wholly or partially produced synthetically. Thus the antibody may be from any appropriate source, for example recombinant sources and/or produced in transgenic micro-organisms, animals or plants. Thus, the antibody molecules may be produced in vitro or in vivo.

In some embodiments, the nucleic acid molecules of the present invention may be cloned or synthesised by any appropriate method and may be incorporated in a known manner into an appropriate expression vector which ensures good expression of the antibodies and fragments of the invention. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors may contain a nucleic acid molecule of the invention and regulatory sequences selected on the basis of the host cells to be used for expression, which are operatively linked to the nucleic acid molecule. Operatively-linked is intended to mean that the nucleic acid is linked to regulatory sequences in a manner which allows expression of the nucleic acid.

In certain embodiments, the invention provides an expression vector comprising a nucleic acid molecule of the invention, or a fragment thereof, operatively linked to regulatory sequences for the transcription and translation of the polypeptide sequence encoded by the nucleic acid molecule of the invention.

Suitable regulatory sequences may be derived from a variety of sources, including bacterial, fungal, viral, mammalian, or insect genes. Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

In certain embodiments, the expression vectors of the invention may also contain a selectable marker gene which facilitates the selection of host cells transformed or transfected with a molecule of the invention. Examples of selectable marker genes are genes encoding a protein such as neomycin and hygromycin which confer resistance to certain drugs, β-galactosidase, chloramphenicol acetyltransferase, firefly luciferase, or an immunoglobulin or portion thereof such as the Fc portion of an immunoglobulin, for example IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors described herein and in particular to determine the effect of a mutation on expression and phenotype. It will be appreciated that selectable markers can be introduced on a separate vector from the nucleic acid of interest.

The expression vectors may also contain genes which encode a fusion moiety which provides increased expression of the antibody protein; increased solubility of the protein; and/or aid in the purification of the target protein by acting as a ligand in affinity purification (for example appropriate "tags" to enable purification and/or identification may be present, e.g. His tags or myc tags). For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant antibody protein.

Expression vectors can be introduced into host cells to produce a transformed host cell. The terms "transformed with", "transfected with", "transformation" and "transfection" are intended to encompass introduction of nucleic acid (e.g. a vector) into a cell by one of many possible techniques known in the art.

The term "transformed host cell" as used herein is intended to also include cells capable of glycosylation that have been transformed with a recombinant expression vector described herein. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989), and other laboratory textbooks.

Furthermore, in certain embodiments, the invention provides a host cell comprising one or more of the expression vectors or one or more of the nucleic acid molecules of the invention, or a host cell expressing one or more of the antibodies or fragments of the invention.

In some embodiments, the host cell is an isolated host cell. Suitable host cells include a wide variety of eukaryotic host cells and prokaryotic cells. For example, in certain embodiments, the antibodies and fragments of the invention may be expressed in yeast cells, fungal cells, insect cells or mammalian cells (e.g. mouse, hamster or human cells).

In certain embodiments, N-terminal or C-terminal fusion proteins comprising the antibodies and fragments of the invention conjugated with other molecules, such as proteins, may be prepared by fusing, through recombinant techniques. In certain embodiments, the resultant fusion proteins contain an antibody of the invention fused to the selected protein or marker protein, or tag protein as described herein. The proteins of the invention may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate. Examples of proteins which may be used to prepare fusion proteins or conjugates include cell binding proteins such as immunoglobulins, hormones, growth factors, lectins, insulin, low density lipoprotein, glucagon, endorphins, transferrin, bombesin, asialoglycoprotein glutathione-S-transferase (GST), hemagglutinin (HA), and truncated myc.

A yet further aspect of the invention provides a method of producing an antibody or antigen-binding fragment of the invention comprising a step of culturing a host cell of the invention.

In certain embodiments, methods comprise the steps of (i) culturing a host cell comprising one or more of the expression vectors or one or more of the nucleic acid molecules of the invention under conditions suitable for the expression of the antibody or fragment; and optionally (ii) isolating the antibody or fragment from the host cell or from the growth medium/supernatant. In certain embodiments, such methods of production may also comprise a step of (iii) purifying the antibody or fragment, and/or (iv) formulating the antibody or fragment into a composition, optionally including at least one additional component, such as a pharmaceutically acceptable carrier or excipient.

Monoclonal antibodies may be prepared using techniques which are well known in the art.

In certain embodiments, the invention also provides a method of obtaining a monoclonal antibody, the method comprising:

(i) immunizing an animal with a peptide whose amino acid sequence comprises amino acids 346-359 of SEQ ID NO: 1 or a peptide substantially homologous thereto, wherein the peptide is optionally attached to a carrier, (ii) obtaining an antibody-producing cell from the animal, wherein the antibody-producing cell produces an antibody which binds to a peptide whose amino acid sequence comprises amino acids 346-359 of SEQ ID NO: 1, and (iii) fusing the antibody producing cell with an immortal cell to produce a hybridoma that produces a monoclonal antibody.

In certain embodiments, the animal is a mammal, for example a mouse, rat, rabbit, goat, donkey or sheep. In certain embodiments, the animal is a mouse, e.g. a BALB/c mouse.

In certain embodiments, antibodies of the invention may also be produced by screening a recombinant library, e.g. a phagemid library.

In some aspects, the invention relates to the use of small nucleic acid molecules, including antisense nucleic acids and short interfering nucleic acid (siNA), the latter include, for example: microRNA (miRNA), short interfering RNA (siRNA), double-stranded RNA (dsRNA), and short hairpin RNA (shRNA) molecules to knockdown expression of target genes. As described herein, RNA interference (RNAi) is a phenomenon describing double-stranded (ds)RNA-dependent gene specific posttranscriptional silencing. Synthetic duplexes of 21 nucleotide RNAs can mediate gene specific RNAi in mammalian cells, without invoking generic antiviral defense mechanisms (Elbashir et al. Nature 2001, 411:494-498; Caplen et al. Proc Natl Acad Sci 2001, 98:9742-9747). In certain embodiment, each strand of the siNA molecule comprises about 19 to about 23 nucleotides, and each strand comprises at least about 19 nucleotides that are complementary to the nucleotides of the other strand. In certain embodiments, the subject RNAi constructs are "siRNAs." These nucleic acids are between about 19-35 nucleotides in length, or 21-23 nucleotides in length, e.g., corresponding in length to the fragments generated by nuclease "dicing" of longer double-stranded RNAs.

The siNA can be unmodified or chemically-modified. The siNA can be chemically synthesized (for example as a short oligonucleotide), expressed from an expression vector (for example linked to a promoter element) or enzymatically synthesized. Short oligonucleotides may, for example, be chemically-modified synthetic short interfering nucleic acid (siNA) molecules capable of modulating gene expression or activity in cells by RNA interference (RNAi). The use of chemically-modified siNA improves various properties of native siNA molecules through, for example, increased resistance to nuclease degradation in vivo and/or through improved cellular uptake. Furthermore, siNA having multiple chemical modifications may retain its RNAi activity. There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2'-O-methyl, 2'-H, nucleotide base modifications. Sugar modification of nucleic acid molecules have been extensively described in the art.

Production of polynucleotides comprising RNAi sequences is well known in the art. For example, polynucleotides comprising RNAi sequences can be produced by chemical synthetic methods or by recombinant nucleic acid techniques. The siRNA molecules can be purified using a number of techniques known to those of skill in the art. For example, gel electrophoresis can be used to purify such molecules. Alternatively, non-denaturing methods, such as non-denaturing column chromatography, can be used to purify the siRNA molecules. In addition, chromatography (e.g., size exclusion chromatography), glycerol gradient centrifugation, affinity purification with antibody can be used to purify siRNAs.

In some embodiments, one of the strands of the double-stranded siNA molecule comprises a nucleotide sequence that is complementary to a nucleotide sequence of a target RNA or a portion thereof, and the second strand of the double-stranded siNA molecule comprises a nucleotide sequence identical to the nucleotide sequence or a portion thereof of the targeted RNA. In another embodiment, one of the strands of the double-stranded siNA molecule comprises a nucleotide sequence that is substantially complementary to a nucleotide sequence of a target RNA or a portion thereof, and the second strand of the double-stranded siNA molecule comprises a nucleotide sequence substantially similar to the nucleotide sequence or a portion thereof of the target RNA. In certain embodiments, the number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are important and may abolish cleavage of the target RNA. In contrast, nucleotides at the 3' end of the siRNA strand that is complementary to the target RNA do not significantly contribute to specificity of the target recognition. An RNAi construct contains a nucleotide sequence that hybridizes under physiologic conditions of the cell to the nucleotide sequence of at least a portion of the mRNA transcript of a gene of interest. In certain embodiments, the double-stranded RNA need only be sufficiently similar to natural RNA that it has the ability to mediate RNAi. In certain embodiments, sequence identity may be optimized by sequence comparison and alignment algorithms known in the art (see Gribskov and Devereux, Sequence Analysis Primer, Stockton Press, 1991) and calculating the percent difference between the nucleotide sequences by, for example, the Smith-Waterman algorithm as implemented in the BEST-FIT software program using default parameters (e.g., University of Wisconsin Genetic Computing Group). In certain embodiments, the sequence identity between the inhibitory RNA and the portion of the target gene is greater than 85%, 86%, 87%, 88%, 89%, 90%, 91%, 92%, 93%, 94%, 95%, 96%, 97%, 98%, 99%, or is 100%. Tools for design and quality of siRNAs, shRNAs and/or miRNAs are known in the art. Web-based online software system for designing siRNA sequences and scrambled siRNA sequences are for example siDirect, siSearch, SEQ2SVM, Deqor, siRNA Wizard (InvivoGen). The specificity can be predicted using for example SpecificityServer, miRacle. Target sequences can be researched for example at HuSiDa (Human siRNA Database), and siRNAdb (a database of siRNA sequences).

In certain embodiments, siNA molecules, as described herein, are provided that specifically target ADAM-15 protein expression by inducing RNA interference (RNAi).

It should be appreciated that ADAM-15 specific siNA molecules (such as siRNA molecules) may be used for any method of treatment provided herein alone or in combination with the antibodies or fragments thereof or with the immunogenic peptides, described herein.

In certain embodiments, the invention provides a composition comprising an antibody or antigen-binding fragment thereof of the invention, together with one or more pharmaceutically acceptable excipients, carriers, diluents, buffers or stabilizers.

In certain embodiments, compositions are provided comprising an antibody or antigen-binding fragment thereof, as described herein, and further comprising a nucleic acid molecule capable of inducing RNA interference (RNAi), such as short interfering nucleic acid (siNA) molecules, further optionally comprising one or more pharmaceutically acceptable excipients, carriers, diluents, buffers or stabilizers.

In certain embodiments, the compositions of the present invention can be formulated according to any of the conventional methods known in the art and widely described in the literature. Thus, the active ingredient (e.g. the antibody or antigen-binding fragment thereof, siNA molecules and/or immunogenic peptides) may be incorporated, optionally together with other active substances (examples of which are as described below), with one or more conventional pharmaceutically acceptable carriers, diluents and/or excipients, etc., appropriate for the particular use for a composition, to produce conventional preparations which are suitable or can be made suitable for administration. They may be formulated as liquids, as semi-solids or as solids, e.g. liquid solutions, dispersions, suspensions, tablets, pills, powders, sachets, cachets, elixirs, emulsions, syrups, ointments, liposomes, suppositories, and the like, depending on the intended mode of administration and therapeutic application. In some embodiments, the composition comprising, for example an antibody or antigen-binding fragment thereof, or an immunogenic peptide or an siRNA or any combination thereof, described herein, is prepared in a form of an injectable or infusible solution.

In some embodiments, the mode of administration is parenteral, e.g. intraperitoneal, intravenous, subcutaneous, intramuscular, intracavity or transdermal, although any other appropriate mode may be used, for example oral administration. In certain embodiments, intravenous injection or infusion may be used. Any appropriate site of administration may be used. For example they may be administered locally and directly at the site where action is required or may be attached or otherwise associated, e.g. conjugated, with entities which will facilitate the targeting to an appropriate location in the body.

In certain embodiments, any physiologically compatible carrier, excipient, diluent, buffer or stabilizer can be used in the compositions of the invention. Examples of suitable carriers, excipients, diluents, buffers and stabilizers include one or more of water, saline, phosphate buffered saline, dextrose, glycerol, ethanol and the like, as well as combinations thereof. In some cases isotonic agents, e.g. sugars, polyalcohols (e.g. mannitol, sorbitol), or sodium chloride may be included. The compositions may additionally include lubricating agents, wetting agents, emulsifying agents, suspending agents, preserving agents, sweetening agents, flavouring agents, and the like. In certain embodiments, the compositions of the invention may be formulated so as to provide quick, sustained or delayed release of the active ingredient after administration to the subject by employing procedures well known in the art. As described above, in certain embodiments, the composition is in a form suitable for injection and suitable carriers may be present at any appropriate concentration, but exemplary concentrations are from 1% to 20% or from 5% to 10%.

Therapeutic compositions typically must be sterile and stable under conditions of manufacture and storage. Appropriate ways of achieving such sterility and stability are well known and described in the art.

In certain embodiments, in addition to an antibody or antigen-binding fragment thereof described herein, the composition may further comprise one or more other active ingredients such as other agents which are useful for treating cancers, in particular breast cancer. Suitable additional active agents for inclusion in a composition that is to be used in the treatment of mammals will be known to a person skilled in the art and can be selected depending on the nature of the disease which is to be treated by the composition. Suitable additional agents include antibodies which bind to other targets, cytokines, and chemical agents, e.g. standard chemotherapeutics (small molecule drugs) or drugs controlling side effects. For breast cancer treatment suitable additional agents might include Herceptin, Doxil (Doxorubicin), Avastin or Taxotere.

In some embodiments, combined anti-angiogenic formulations are provided, e.g. combining an antibody or antigen-binding fragment of the invention with an anti-antiangiogenic agent, e.g. a angiopoietin, angiostatin and/or endostatin.

Suitable doses of the antibody or antigen-binding fragment thereof of the invention and the other active ingredients (if included) will vary from patient to patient and will also depend on the nature of the particular disease. In some embodiments, said dosages constitute a therapeutically effective amount or a prophylactically effective amount, depending on the nature of the treatment involved. Suitable doses can be determined by the person skilled in the art or the physician in accordance with the weight, age and sex of the patient and the severity of the disease. The ability of the binding protein to elicit a desired response in the individual will also be a factor. Exemplary daily doses are: 0.1 to 250 mg/kg, or 0.1 to 200 or 100 mg/kg, or 1 to 50 or 1 to 10 mg/kg, of the active ingredient. This can be administered as a single unit dose or as multiple unit doses administered more than once a day. It is to be noted however that appropriate dosages may vary depending on the patient and that for any particular subject, specific dosage regimes should be adjusted over time according to the individual needs of the patient. Thus, the dosage ranges set forth herein are to be regarded as exemplary and are not intended to limit the scope or practice of the claimed composition.

In certain embodiments, the invention further provides kits comprising one or more of the antibodies or antigen-binding fragments or compositions of the invention or one or more of the nucleic acid molecules encoding the antibodies or antigen-binding fragment of the invention, or one or more expression vectors comprising the nucleic acid molecules of the invention, or one or more host cells comprising the expression vectors or nucleic acid molecules of the invention. In some embodiments, said kits are for use in the methods and uses as described herein, e.g. the therapeutic, diagnostic or imaging methods as described herein, or are for use in the in vitro assays or methods as described herein. The antibodies/fragments in such kits may, in some embodiments, be an antibody conjugate as described herein, e.g. may be conjugated to a detectable moiety. In some embodiments, said kits comprise instructions for use of the kit components, for example in diagnosis.

In some embodiments, said kits are for diagnosing cancer and optionally comprise instructions for use of the kit components to diagnose cancer.

In certain embodiments, the invention further provides a kit for diagnosing cancer comprising one or more of the antibodies or antigen-binding fragments thereof of the invention and optionally instructions for the use thereof to diagnose the cancer. In certain embodiments, the invention also provides a kit for diagnosing cancer comprising an antibody or antibody fragment as described herein, and optionally instructions for the use thereof to diagnose cancer.

In certain embodiments, the invention also provides methods involving the antibodies of the invention. It will be noted, however, that the methods described herein are not limited to the antibodies described above. In certain embodiments, the methods of the invention do not exclude the use of rabbit polyclonal antibodies.

In certain embodiments, the invention also provides a method of inhibiting or preventing angiogenesis comprising administering to a patient a therapeutically effective amount of an antibody or antigen-binding fragment which specifically recognises the metalloprotease domain of the human ADAM 15 polypeptide.

In certain embodiments, the antibody or antigen-binding fragment is an isolated antibody or antigen-binding fragment thereof which specifically binds to a peptide comprising or consisting of the amino acid sequence:

```
       IAHELGHSLGLDHD        (SEQ ID NO: 3)
``` or a peptide with at least 70%, or at least 80% or 90%, sequence identity to SEQ ID NO: 3.

In other embodiments, the antibody or antigen-binding fragment is an isolated antibody or antigen-binding fragment thereof which specifically binds to an epitope on human ADAM 15 polypeptide defined by amino acids 346-359 of SEQ ID NO: 1.

In other embodiments, the antibody or antigen-binding fragment is an isolated antibody or antigen-binding fragment thereof which specifically binds to human ADAM 15 polypeptide, and wherein the antibody or antigen-binding fragment thereof binds to the ADAM 15 epitope defined by amino acids 346-359 of SEQ ID NO: 1 such that the antibody prevents proteolytic cleavage of the urokinase receptor uPAR by ADAM 15.

In yet other embodiments, the antibody or antigen-binding fragment is an isolated antibody or antigen-binding fragment thereof which specifically binds to an epitope on human ADAM 15 polypeptide defined by the topographic region $His^{352}$, $Ser^{353}$, $Leu^{354}$, $Gly^{355}$, $Leu^{356}$, $Asp^{357}$ and $Asp^{359}$, or an isolated antibody or antigen-binding fragment thereof which specifically binds to an epitope on human ADAM 15 polypeptide defined by the topographic region $Leu^{354}$, $Gly^{3'''}$, $Leu^{3'''}$, $Asp^{357}$, $His^{358}$ and $Asp^{359}$.

In other aspects, the invention provides a method of inhibiting or preventing endothelial cell proliferation in a patient comprising administering to said patient a therapeutically effective amount of an antibody or antigen-binding fragment thereof as defined herein.

In certain embodiments, the invention also provides a method of inhibiting or preventing neovascularization comprising administering to a patient a therapeutically effective amount of an antibody or antigen-binding fragment thereof as defined herein.

In certain embodiments, the invention further provides a method of inhibiting or preventing neovascularization and/or angiogenesis in a tumour comprising administering to a patient or to the tumour a therapeutically effective amount of an antibody or antigen-binding fragment thereof as defined herein.

In certain embodiments, the invention further provides a method of inhibiting the spread of a tumour in a patient comprising administering to a patient or to the tumour a therapeutically effective amount of an antibody or antigen-binding fragment thereof as defined herein.

In certain embodiments, the invention further provides a method of treating cancer in a patient comprising administering to said patient a therapeutically effective amount of an antibody or antigen-binding fragment thereof as defined herein.

In certain embodiments, the invention further provides a method of treating acute macular degeneration in a patient comprising administering to said patient a therapeutically effective amount of an antibody or antigen-binding fragment thereof as defined herein.

In certain embodiments, the invention further provides a method of treating diabetic retinopathy and/or proliferative retinopathy in a patient comprising administering to said patient a therapeutically effective amount of an antibody or antigen-binding fragment thereof as defined herein.

Associated systemic and ocular diseases include sickling hemoglobinopathies, branch retinal vein obstruction, diabetes mellitus, sarcoidosis, intravenous drug abuse, the ocular ischemic syndrome, pars planitis, Coats' disease and retinitis pigmentosa/retinal detachment. In certain embodiments, the invention relates to the treatment of such disease also.

In certain embodiments, the invention further provides a method of treating inflammatory bowel disease (IBD) in a patient comprising administering to said patient a therapeutically effective amount of an antibody or antigen-binding fragment thereof as defined herein.

In certain embodiments, the invention further provides a method of treating Crohn's Disease in a patient comprising administering to said patient a therapeutically effective amount of an antibody or antigen-binding fragment thereof as defined herein.

In certain embodiments, the invention further provides a method of treating arthritis, for example rheumatoid arthritis or osteoarthritis, in a patient comprising administering to said patient a therapeutically effective amount of an antibody or antigen-binding fragment thereof as defined herein.

In certain embodiments, the invention further provides a method of treating an inflammatory vascular disorder, for example restenosis and/or atherosclerosis, in a patient comprising administering to said patient a therapeutically effective amount of an antibody or antigen-binding fragment thereof as defined herein.

In certain embodiments, the invention provides a methods of treating a subject comprising administering an effective amount of an antibody or antigen-binding fragment thereof as defined herein to a biological sample (e.g. a blood sample) removed from the subject, wherein the sample is subsequently returned to the subject.

In certain embodiments, the invention also relates to a method of producing anti-ADAM15 antibodies in human patient, the method comprising administering to said patient a peptide comprising or consisting of the amino acid sequence:

```
       X1-IAHELGHSLGLDHD-X2    (SEQ ID NO: 8)
``` wherein X1 is an N-terminal protecting group, optionally absent,

X2 is a C-terminal protecting group, optionally absent, or a peptide with at least 70%, or at least 80% or 90%, sequence identity to SEQ ID NO: 8, wherein the peptide is optionally bound to a carrier, optionally in admixture with one or more adjuvants, diluents and/or excipients.

Examples of the N-terminal protecting group, X1, include Ac and 1-5 amino acids. Examples of the C-terminal protecting group, X2, include $NH_2$ and 1-5 amino acids.

In certain embodiments, the invention also relates to a method of treating a disorder as defined herein, comprising the steps of the method of producing anti-ADAM15 antibodies as defined above.

In certain embodiments, the present invention may be used to treat animals and patients with aberrant angiogenesis, such as that contributing to a variety of diseases and disorders. The most prevalent and/or clinically important of these, outside the field of cancer treatment, include arthritis, rheumatoid arthritis, psoriasis, atherosclerosis, diabetic retinopathy, age-related macular degeneration, Grave's disease, vascular restenosis, including restenosis following angioplasty, arteriovenous malformations (AVM), meningioma, hemangioma and neovascular glaucoma. Other potential targets for intervention include angiofibroma, atherosclerotic plaques, corneal graft neovascularization, hemophilic joints, hypertrophic scars, osler-weber syndrome, pyogenic granuloma retrolental fibroplasia, scleroderma, trachoma, vascular adhesions, synovitis, dermatitis, various other inflammatory diseases and disorders, and endometriosis. In certain embodiments, the invention provides antibodies and antigen-binding fragments thereof of the invention or as disclosed herein for the treatment of such diseases.

In other embodiments, the invention therefore provides antibodies and antigen-binding fragments thereof of the invention or as disclosed herein for the treatment of inflammatory conditions including Inflammatory Bowel Disease, Crohn's Disease, rheumatoid or osteoarthritis.

Methods as described herein (for example, treatment, in vivo methods, and the like) are generally carried out in a mammal. Any mammal may be treated, for example humans and any livestock, domestic or laboratory animal. Specific examples include mice, rats, pigs, cats, dogs, sheep, rabbits, cows and monkeys. In some embodiments, the mammal is a human.

The terms "therapy" or "treatment" as used herein include prophylactic therapy, which may result in the prevention of disease. The terms "therapy", "treatment" and "treating" include combating or cure of disease but also include the controlling, reduction or alleviation of disease or one or more of the symptoms associated therewith.

An "effective amount" as used herein can refer to a therapeutically effective amount or a prophylactically effective amount depending on the nature of the treatment. A therapeutically effective amount can be considered to be an amount necessary (at appropriate dosages and administration regimes) to achieve the desired therapeutic result. A prophylactically effective amount can be considered to be an amount necessary (at appropriate dosages and administration regimes) to achieve the desired prophylactic result. The amounts of the antibody or antigen-binding fragment of the invention are likely to vary depending on the weight, age and sex of the patient, the severity of the disease and the ability of the binding protein to elicit a desired response in the individual.

In one embodiment of the invention, cancer includes, without limitation, cervical cancer, uterine cancer, ovarian cancer, pancreatic cancer, kidney cancer, gallbladder cancer, liver cancer, head and neck cancer, squamous cell carcinoma, gastrointestinal cancer, breast cancer (such as carcinoma, ductal, lobular, and nipple), prostate cancer, testicular cancer, lung cancer, non-small cell lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer (e.g. astrocytoma, glioblastoma, medulloblastoma), neuroblastoma, sarcomas, colon cancer, rectum cancer, stomach cancer, anal cancer, bladder cancer, pancreatic cancer, endometrial cancer, plasmacytoma, lymphomas, retinoblastoma, Wilm's tumour, Ewing sarcoma, melanoma and other skin cancers. In certain embodiments, the cancers are breast cancer, prostate cancer, lung cancer, ovarian cancer, colon cancer, kidney cancer and brain cancer (in particular glioblastoma).

In certain embodiments, the invention provides a method of treating metastatic carcinoma of the colon or rectum in a patient comprising administering to said patient a therapeutically effective amount of an antibody or antigen-binding fragment thereof of the invention or as defined herein. In certain embodiments, the antibody or antigen-binding fragment thereof is administered simultaneously, separately or sequentially with 5-fluorouracil and/or AVASTIN® (Bevacizumab).

In certain embodiments, the invention provides a method of treating recurrent or metastatic non-squamous, non-small cell lung cancer in a patient comprising administering to said patient a therapeutically effective amount of an antibody or antigen-binding fragment thereof of the invention or as defined herein. In certain embodiments, the antibody or antigen-binding fragment thereof is administered simultaneously, separately or sequentially with carboplatin and/or paclitaxel and/or AVASTIN® (Bevacizumab).

Any reference herein to "cancer" or "tumour" should be understood to include a reference to any of the cancer types listed above.

In certain embodiments, cancer cells may be evaluated to determine their susceptibility to the treatment methods of the invention by, for example, obtaining a sample of the cancer cells from a subject and determining the ability of the cancer cells in the sample to bind to the antibodies or antibody fragments of the invention or as described herein.

In certain embodiments, the present invention provides diagnostic methods, agents, and kits that can be used by themselves, or prior to, during or subsequent to the therapeutic method of the invention in order to determine whether or not cancer cells are present that express the antigen and can bind to the antibodies and antibody fragments of the invention.

Widely accepted functional assays of angiogenesis and, hence, anti-angiogenic agents are the corneal micropocket assay of neovascularization and the chick chorio-allantoic membrane assay (CAM) assay. Retinopathy of prematurity (ROP) U.S. Pat. No. 5,712,291 is specifically incorporated herein by reference to show that the corneal micropocket and CAM assays are sufficiently predictive to identify agents for use in the treatment of an extremely wide range of angiogenic diseases.

Yet further aspects are methods of diagnosis or imaging of a subject comprising administering an appropriate amount of an antibody or antigen-binding fragment of the invention or as defined herein to the subject and detecting the presence and/or amount and/or the location of the said antibody or antigen-binding fragment in the subject.

In certain embodiments, appropriate diseases to be treated, imaged or diagnosed in accordance with the above described uses and methods include any disease associated with molecules recognised by the antibody or antigen-binding fragment of the invention, for example cancer and the other diseases mentioned herein.

In certain embodiments, the invention provides a method of diagnosing a disease, for example cancer, in a mammal comprising the step of:

(1) contacting a test sample taken from said mammal with any one or more of the antibodies or antigen-binding fragments thereof of the invention or as disclosed herein.

In a further embodiment, the invention provides a method of diagnosing disease, for example cancer, in a mammal comprising the steps of:

(1) contacting a test sample taken from said mammal with one or more of the antibody or antigen-binding fragment of the invention or as disclosed herein;

(2) measuring the presence and/or amount and/or location of binding protein-antigen complex in the test sample; and, optionally (3) comparing the presence and/or amount of binding protein-antigen complex in the test sample to a control.

In the above methods, said contacting step is carried out under conditions that permit the formation of a binding protein-antigen complex. Appropriate conditions can readily be determined by a person skilled in the art.

In the above methods any appropriate test sample may be used, for example biopsy cells, tissues or organs suspected of being affected by cancer, histological sections or blood.

In the above methods the presence of an amount of binding protein-antigen complex in the test sample would be indicative of the presence of cancer cells. For a positive diagnosis to be made, generally the amount of binding protein-antigen complex in the test sample is greater than, or significantly greater than, the amount found in an appropriate control sample.

In certain embodiments, the significantly greater levels are statistically significant, for example with a probability value of <0.05. Appropriate methods of determining statistical significance are well known and documented in the art and any of these may be used.

Appropriate control samples could be readily chosen by a person skilled in the art, for example, in the case of diagnosis of a particular disease, an appropriate control would be a sample from a subject that did not have that disease.

In certain embodiments, the amount of antibodies or antibody fragments of the invention is measured by measuring the amount of antibodies/fragments of the invention in the test sample, for example by ELISA. In another embodiment, the amount of antibodies of the invention is measured by measuring the expression levels of nucleic acids encoding the antibodies of the invention in the test sample, for example by RT-PCR.

In certain embodiments, the invention also provides diagnostic or imaging agents comprising the antibodies or antibody fragments of the invention or as disclosed herein attached to a label that produces a detectable signal, directly or indirectly.

The antibodies and antigen-binding fragments may be labelled with a detectable marker such as a radio-opaque or radioisotope, such as $^3$H, $^{14}$C, $^{32}$P, $^{35}$S, $^{123}$I, $^{125}$I, $^{131}$I; a radioactive emitter (e.g. $\alpha$, $\beta$ or $\gamma$ emitters); a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion; or a chemical moiety such as biotin which may be detected by binding to a specific cognate detectable moiety, e.g. labelled avidin/streptavidin. Methods of attaching a label to an antibody or antibody fragment, are well known in the art. Such detectable markers allow the presence, amount or location of antibody/fragment-antigen complexes in the test sample to be examined.

In certain embodiments, the invention also provides a method for screening for antibodies which are capable of inhibiting endothelial cell proliferation, the method comprising the steps:

(i) determining the binding affinity or avidity of a test antibody for the metalloprotease domain of ADAM 15, (ii) comparing the affinity or avidity of the test antibody with that of an antibody of the invention or as disclosed herein, wherein a test antibody which has an affinity or avidity which is about the same or higher than that of an antibody of the invention or as disclosed herein is capable of inhibiting endothelial cell proliferation.

EXAMPLES

Example 1

Materials and Methods

Reagents

A human ADAM 15 cDNA clone was kindly provided by Dr Carl Blobel (Cornell University, NY). A canine ADAM 12 cDNA was isolated from a canine smooth muscle cell library by standard oligonucleotide hybridization followed by subcloning into expression vectors (see below). uPAR polyclonal and monoclonal antibodies were obtained from R&D systems, siRNA were produced using the Silencer™ construction kit (Ambion) according to the manufacturer's instructions. ADAM 15 specific primers sets were 5'AACTCCATCTGTTCTCCTGACTTCCTGTCTC 3' (SEQ ID NO: 4) for the sense template and 5' AAAAGTCAG-GAGAACAGATGGAGCCTGTTCTC 3' (SEQ ID NO: 5) for the antisense template. Control siRNAs were generated using the primer sets 5'AAGCCCTTCCTTCCAGTTAC-CTTTCCTGTCTC 3' (SEQ ID NO: 6) for the sense template and 5' AAAAAGGTAACTGGAAGGAAGGCCCTGTCTC 3' (SEQ ID NO: 7) for the antisense template. Anti-uPAR antibodies used were from R&D Systems, Oxon UK, a monoclonal (no MAB807) and a polyclonal (no AF807).

Generation of Anti-Peptide Antibodies

A peptide immunogen aimed to target antibody binding to the substrate binding cleft of the ADAM 15 MP domain was identified through the construction of a molecular model of the MP domain using ProMod II software (SWISS PRO) and the crystal structure of Adamalysin II as a template (26). The peptide designated P15 corresponding to amino acids 346-359 of human ADAM 15 was conjugated to a carrier immunogen (KLH) and injected into rabbits as adjuvants (Sigma-Genosys). Antisera were characterised for reactivity towards both peptide and parent antigen (ADAM 15) and specific antibodies were purified by affinity chromatography using P15-Sepharose columns.

In Vivo Angiogenesis Studies

Intraocular injections were performed on 3 days (P3) old C57/Bl6 mouse pups as described previously (3). Eyes were injected with 5 ng of affinity purified Abs 576 (n=8) or 577 (n=12) or control non-immune rabbit IgG. (n=6). Eyes were enucleated after 48 h, fixed in 4% paraformaldehyde over night. Retinas were dissected out and incubated with biotinylated isolectin B4 (1:10 dilution, lectin from *Griffonia simplicifolia*, Sigma, CA, USA) followed by Alexa 488 streptavidin (Molecular Probes no. S11223) to visualize blood vessels. Proliferating endothelial cells were detected by double labelling by isolectin and polyclonal rabbit anti-phospho-Histone H3 antibodies (1:200; Upstate, Lake Placid, N.Y., no. 06-570) visualized by Alexa 568 conjugated goat-anti-rabbit antibody (Molecular Probes no. A11034). Filopodia number was measured (n=4/treatment), branch points counted (n=4/treatment) and the number of proliferating endothelial cells (n=3/treatment) in 2-6 fields/retina using the image-analysis software ImageJ on images taken with a ZEISS confocal microscope (Axiovert 200) using a 40× objective. Whole mount immunohistochemistry of untreated normal P5 mouse retinas was performed as described previously (3). Endothelial cells were detected with isolectin as described above and uPAR by polyclonal goat-anti uPAR (2 μg/ml; R&D systems no. AF807) followed by Alexa 568 conjugated.rabbit anti-goat antibody (Molecular Probes no. A11079)

In Vitro Endothelial Cell Assays

In vitro cell proliferation and migration assays were performed as described previously (23). Briefly, human dermal microvessel endothelial cells (HMVEC) were maintained in EBM-2 growth medium (Clonetics Corp). Migration studies were carried out essentially as described previously (24) using serum starved Calcein AM-loaded HMVEC in a modified Boyden chamber assay using Fluoroblok transwell chambers (BD Bioscience) as described by the manufacturer. Cell migration was detected by fluorescence measurement (within the lower chamber compartment). Membranes of transwell chambers were coated with Fn (10 µg/ml) overnight at 4° C. For antibody studies, HMVECs were pre-treated with Abs 576 or 577 affinity purified antibodies for 30 min at room temperature prior to application to the upper transwell chamber. For RNA interference studies, HMVECs were transfected with ADAM 15 and control siRNA using Lipofectamine (Invitrogen, Paisely, UK) 72 hours prior to the experiment (this period was determined as the optimal period for knockdown ADAM 15 mRNA see FIG. 1 supp.). For proliferation experiments, cell division was measured by either fluorescence labelling of DNA (CyQuant, Molecular Probes) or by counting cells directly using a microscope fitted with a grid embossed eyepiece. HMVECs were plated on 24-well plates and cultured overnight in EBM-2 medium containing 5% FBS. After washing plates with PBS, HMVECs were then serum starved and then treated with and without VEGF A (50 ng/ml) in the presence of Ab 576 or 577 or control IgG for antibody inhibition studies for 48 hours. Cell numbers were then determined. For RNA interference studies, HMVECs were transfected with ADAM 15 and control siRNA's 72 hours prior to serum starvation and VEGF stimulation.

Immunoprecipitation Studies Western Blotting and Zymography

Immunoprecipitation studies were performed as described previously (23). Briefly, human microvessel endothelial cells (HMVEC) in serum-free MCDB-131 medium (BioWhittaker) supplemented with 0.1% BSA were plated on uncoated petri dishes in the absence or presence of VEGF A (50 ng/ml) for 15 to 120 minutes at room temperature. Cells were then harvested in a Triton X-100 based lysis buffer and immunoprecipitation was performed with a rabbit monoclonal antibody (Cell Signalling Laboratories) to VEGFR2 or a monoclonal uPAR (R&D Systems no MAB807). After analysis by SDS-PAGE and protein transfer, the blot was then probed with anti ADAM 15 MP domain antibodies Ab 576 or Ab 577 or a mixture of both reagents and developed by chemiluminescence. For native Western blotting, samples were electrophoretically transferred in Tris-glycine buffers without SDS. Denaturation of proteins on PVDF membranes was achieved by incubation in 0.2M NaOH for 15 min at room temperature prior to the blocking step. Casein zymography was performed as follows. Tris-glycine SDS-PAGE gels were made containing casein (3 mg/ml) and Lys-plasminogen (10 µg/ml) (Enzyme research Laboratories, Swansea, UK no LPG2002). After electrophoresis under non-reducing conditions, the gels were washed in 2.5% Triton X-100 and incubated in 0.1 M glycine (pH 8.3) for 15 hours at 37° C. Gels were then stained with Coommassie blue and zones of lysis were assessed for relative activity using NIH Image software. For semi-quantative analysis of blots, autoradiorahs were scanned and relative band intensities were quantified by NIH Image software.

Measurement of Urokinase Activity

A whole cell urokinase activity assay was performed essentially as described previously (25). U937 cells were selected for stable transfection with ADAM 15 cDNA after a screen of cell lines by Western blotting showed no expression of the antigen (see FIG. 1F). Cells were transfected with pcDNA3 containing ADAM 15 cDNA insert using lipofection. Stable transfectants were isolated by repetitive dilution and selection with antibiotic selection using G418 at 400 ug/ml and western blotting for ADAM 15 antigen to monitor expression. U937 cells stably transfected with pcDNA3-ADAM 15 or control cells were grown in RPMI complete medium supplemented with 10% (v/v) foetal bovine serum to a density of approx. $1 \times 10^6$/ml. Cells were harvested and washed in PBS, pH 7.4. Cells were then given a brief acidic wash in 0.1M glycine pH 3.0 for 1-2 min to remove endogenous cell associated urokinase, followed by a further wash and final resuspension in Tris-saline pH 7.4 at $1 \times 10^6$/ml. Cells were then incubated on ice with 2 nM Pro-uPA (Calbiochem UK no 672112) for 30 min in the presence or absence of 10 nM PAI-1 (Calbiochem no 528205). The assay was initiated by addition of 200 ul of the cell suspension to microtiter wells preloaded with the urokinase specific fluorogenic substrate Z-Gly-Gly-Arg-AMC.HCl (Calbiochem, UK no 672159), at a final concentration of 200 µM. The reaction was followed for 30 min with readings taken every 2 min at 355/460 nm excitation/emission. Background levels of substrate hydrolysis were measured by inclusion In Vitro Protease Reaction Recombinant ADAM 15 and canine ADAM 12 MP domains were generated as GST-fusion proteins using an insect cell expression system. ADAM 15 and 12 MP domain constructs were generated by PCR from their respective cDNA clones and subcloned into a modified pMT vector (Invitrogen, Paisely UK) containing a GST tag positioned N-terminal to the MP domain inserts. Sf2 cells (Invitrogen, Paisley, UK), stably transfected with ADAM 15 and 12 MP constructs, were cultured in Scheider's medium (Invitrogen) supplemented with 10% (v/v) FBS plus 100 ug/ml blasticidin (Invitrogen, Paisely, UK). Gene expression was induced by addition of 500 uM $Cu_2SO_4$ for a period of 24 hours after which the cellular fraction was processed for recombinant GST-ADAM 15 and 12 MP domain purification by affinity chromatography using glutathione-Sepharose. For the in vitro protease reaction, 100 ng of purified recombinant soluble uPAR (R&D systems, UK, no 807-UK/CF) was incubated with 1.0 ng of recombinant GST-ADAM 15 MP domain or GST-ADAM 12 MP domain for varying lengths of time in the buffer 25 mM HEPES pH 7.4, 150 mM NaCl, 0.005% Brj 35, 1 mM $CaCl_2$, 50 µM $ZnCl_2$. The reaction was stopped by the addition of Laemmli buffer and the samples evaluated by Western blotting probing with a uPAR monoclonal (R&D systems no MAB807).

Example 2

Development of Function Blocking Site-Directed Antibodies to ADAM 15

To facilitate a rational design of a peptide immunogen for the development of a function-blocking site-directed antipeptide antibody towards the ADAM 15 MP domain, a molecular model of the ADAM 15 MP domain was constructed using the crystal structure of the snake venom disintegrin-metalloprotease Adamalysin II (26).

FIG. 1. shows the development and characterisation of ADAM 15 MP domain site-specific antibodies. Panel A-A molecular model of the ADAM 15 metalloprotease domain was constructed using ProModII (Swiss-Model). Ribbon diagram of a 2 Å structure of adamalysin II complexed with a peptide phosphonate inhibitor. Histidine side chains in the catalytic cleft are marked (1) coordinating a Zinc atom (2). The phosphonate peptide is marked (3) in the a space filling model. Opposite to this active-site cleft is an integrated calcium ion (4) coordinated by carbonyl and strongly conserved carboxylate/carboxamide residues.

Panel B—molecular model of ADAM 15 metalloprotease domain showing a highly conserved structure with histidine side chains in the catalytic cleft shown as red ball and stick structure. The region of the catalytic cleft encompassing to the epitopes of Abs 576/577 within peptide P-15 is marked as (5) (Ab 577 specific residues), (6) (Ab 576 specific), and (7) (overlapping residues).

Panel C Models from panels A and B are superimposed.

Panel D—Abs 576 and 577 have Distinct Epitopes. Synthetic peptides corresponding to the amino acid sequence 346-359 within the ADAM 15 MP domain were synthesized with consecutive alanine substitutions and (1.0 µg) spotted onto nitrocellulose and processed for blotting with affinity purified Abs 576 and 577. Dot blots were developed by chemiluminescence. Essential amino acid side chains comprising the epitopes for Abs 576 and 577 are shown as bold. Synthetic peptides were synthesized corresponding to the equivalent peptide region of other ADAMs proteins and MMPs and analysed as above for cross-reactivity with Abs 576 and 577. No cross reactivity was observed.

Panel E Abs 576 and 577 cross react with the MP domain of human ADAM 15 (hMP 15) but not the MP domain of canine ADAM 12 (cMP 12). ADAM 15/12 MP domains were generated as GST-fusion proteins in a modified insect cell vector (pSecTag, Invitrogen) and analysed by SDS-PAGE and Western blotting. The blots were probed with the antibodies shown. V5 antibodies (Invitrogen) cross react with both recombinant MP domains.

Panel F U937 cells were transfected with full length ADAM 15 cDNA or control non-transfected cells were obtained by repetitive dilution and antibiotic selection. Cell lysates were analysed by SDS-PAGE and western blotting probing with Ab 576 and 577. Top panel shows samples analysed without SDS in the blotting stage and bottom panel shows the same blots re-probed after alkaline denaturation.

A peptide (p15) corresponding to the sequence Ile346-Asp359 within a β-loop structure located at the mouth of the active site cleft was selected as an appropriate immunogen. Two antisera were generated designated Ab 576 and Ab 577. An alanine scan of p15 showed that Abs 576 and 577 had distinct epitopes located towards the C-terminal region of the peptide. The epitope for Ab 577 was discontinuous and larger than Ab 576 comprising 7 indispensable amino acid side chains (residues His352, Ser353, Leu354, Gly355, Leu356, Asp357 and Asp359) as compared to 6 consecutive amino acids (Leu354-Asp359, FIG. 1D top panel). These antisera were shown to be selective for the ADAM 15 and displayed no detectable cross reactivity to the corresponding regions of several other ADAMs family members or MMPs (FIG. 1D bottom panel). In addition, both Abs 576 and 577 specifically recognized a recombinant ADAM 15 MP domain-GST fusion protein as opposed to an ADAM 12 counterpart and native ADAM 15 antigen expressed in human cell lines and rat tissue homogenates (FIG. 1E). Interestingly, under native blotting conditions, Ab 576 preferentially recognized the inactive precursor zymogen of ADAM 15 corresponding to an antigen of Mr 120 kDa in stably transfected U937 cells expressing full length ADAM 15 (FIG. 1F top panel). In contrast, Ab 577 predominantly recognized the activated metalloprotease corresponding to the 70 kDa antigen in these cell lysates. The differential recognition of the ADAM 15 molecular species by the antibodies suggests that the region Ile346-Asp359 adopts distinct conformations in the precursor and active polypeptides. This was supported by the observation that denaturation of the antigens immobilized on the blots engendered the recognition of both precursor and active molecular species by both antibodies (FIG. 1F bottom panel).

Example 3

ADAM 15 MP Domain Antibodies Dysregulate Angiogenesis

To investigate the role of ADAM 15 in angiogenesis in vivo, we studied the effects of Abs 576 and 577 compared to control IgG on the developing vascular plexus in post-natal mouse retina. Intraocular microinjection of either Abs 576 or 577 into normal mice promoted a dysregulated angiogenic response (FIG. 2 a-f).

Figure 2:
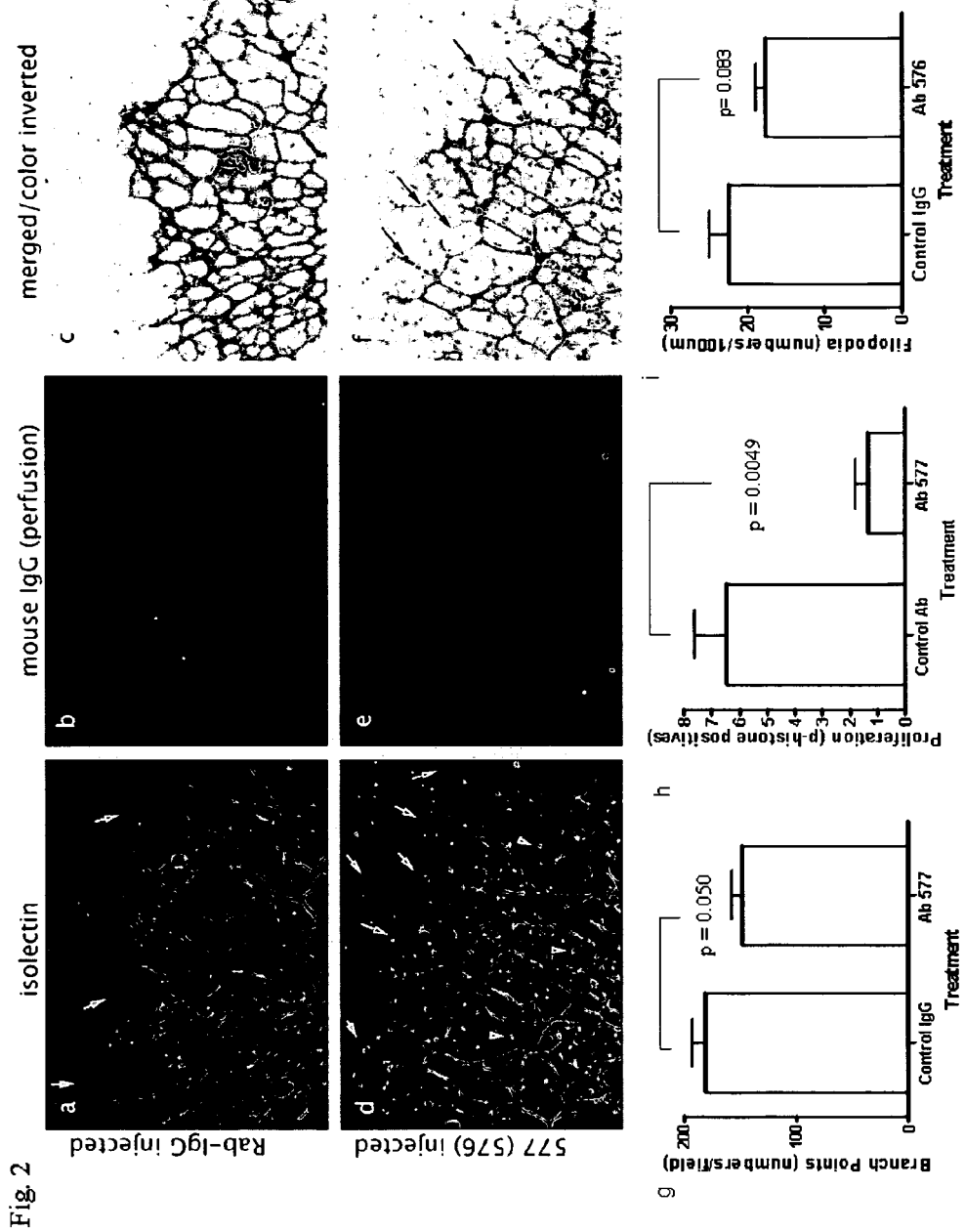
FIG. 2 illustrates non-limiting embodiments of ADAM 15 MP directed antibodies that dysregulate angiogenesis.

FIG. 2 shows ADAM 15 MP directed antibodies dysregulate angiogenesis. (Panels a-f) Whole-mounts of retinas 48 h after intraocular injections with control rabbit-IgG (a-c) and ADAM 15 antibody Ab 576 or Ab 577 (d-f), vessels are detected by isolectin staining (depicted in panels a and d of FIG. 2; stained green in the original experiments) and perfusion with mouse IgG (depicted in panels b and e of FIG. 2; stained red in the original experiments). Merged images with inverted colour to highlight the perfusion of vessels (c, f). Panels (a-c) Normal vascular patterning is seen in control-injected retinas. Panels (d f) ADAM 15 antibody injection leads to morphological changes including increased infiltration of microglia/macrophage cells in the growing front (arrows in a, d) and in the capillary plexus (arrow heads in d), and poor perfusion (arrows in f pointing at non-perfused vessels). (Panels g-i) Quantification of number of branch points (g), proliferating endothelial cells (h), and filopodia (i) showed significantly decreased numbers of branch points and proliferating endothelial cells in ADAM 15 injected retinas but no change in filopodia number compared to control injected retinas.

The vessels that developed during the 48 h exposure period were characterized by reduced branching density, reduced patency and poor perfusion (b c e). ADAM 15 antibody-treated retinas also showed greater numbers of microglial/macrophage cells in the growing front as well as behind in the capillary plexus (arrow heads a, d); a phenotype commonly caused by either excessive vascular leakage or retinal hypoxia (27). Quantification of branchpoints revealed a slight but significant reduction in ADAM 15 antibody-treated specimens (FIG. 2g). However, EC proliferation, assessed by anti-phosphohistone H3 immunofluorescence labelling, was severely impaired in these retinas compared to eyes injected with control IgG (FIG. 2h). Additionally, the vessels appeared very thin and lacked perfusion (absence of luminal serum IgG immunofluorescence, compare FIGS. 2c and f). As branching frequency correlates with the relative number of tip cells, we quantified the density of tip cell filopodia along the leading endothelial membrane. Interestingly, the number of filopodia was not significantly altered, indicating that ADAM 15 MP directed antibodies do not affect VEGF mediated tip cell induction (FIG. 2i). Together, these in vivo observations suggest that ADAM 15 may be primarily involved in cellular functions and signalling pathways required for stalk patency and stalk cell proliferation during angiogenic branching morphogenesis.

Example 4

ADAM 15 Promotes VEGF-Induced Endothelial Cell Proliferation and Survival

To directly investigate the function of ADAM 15 in endothelial cells, we examined the effect of blocking ADAM 15 function in VEGF A stimulated EC (human dermal microvessel endothelial cells, HMVEC) in vitro.

Figure 3:
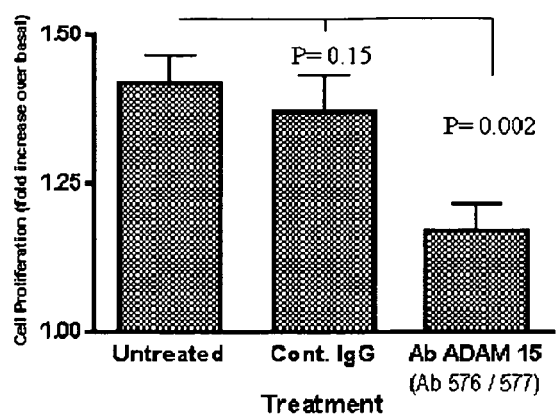
FIG. 3 illustrates the importance of ADAM 15 for VEGF-induced endothelial cell proliferation and cell survival.
Figure 3:
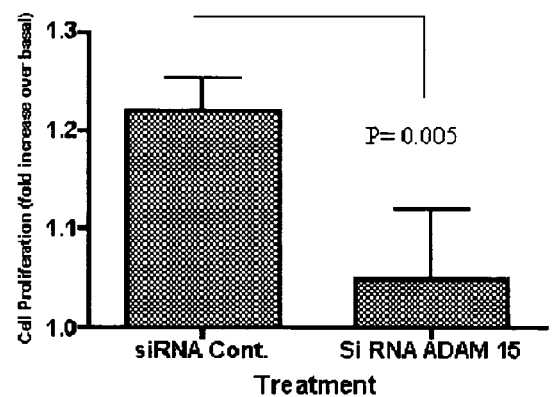
Figure 3:
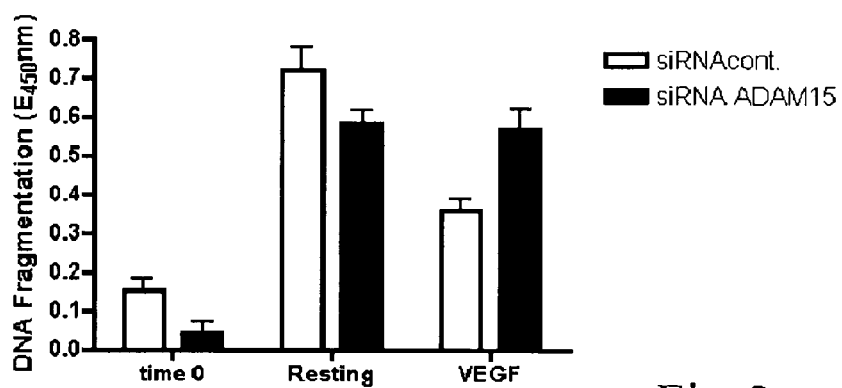

FIG. 3 shows ADAM 15 is important for VEGF-induced endothelial cell proliferation and cell survival.

Panel A-HMVECs monolayers were treated with anti-ADAM 15 antibodies Ab 576 or Ab 577 (top) or ADAM 15 siRNA (bottom) prior analysis for cell proliferation. Proliferation was measured 48 hours post-VEGF stimulation. The data is an average of three separate experiments performed with triplicate wells.

Panel B Cell survival measured by assessing DNA fragmentation at 6 hours post serum depletion in the presence or absence of VEGF-A as shown. Studies were performed in triplicate wells (n=3).

Cell division in samples treated with Ab 576 (or Ab 577 not shown) was significantly reduced (approx. 73%) in response to stimulation with VEGF after 48 hours compared to cell monolayers treated with non-immune IgG (FIG. 3A top panel). Similarly, endothelial monolayers treated with siRNA specific for ADAM 15 also showed a dramatic reduction (>90%) in proliferation in response to VEGF A stimulation compared to cells treated with control siRNA (FIG. 3A bottom panel). To check whether loss of ADAM 15 function was inducing apoptosis, DNA fragmentation in these samples was measured. Treatment of endothelial cells with ADAM 15 siRNA's in full serum condition did not induce apoptosis even after 72 hours of treatment (FIG. 3B, time=0). However, serum depletion rapidly induced DNA fragmentation (after 6 hours) in both control and siRNA ADAM 15 treated cells. Adding VEGF A into the medium significantly protected control siRNA treated cells, but not ADAM 15 siRNA treated cells from apoptosis induced by serum deprivation (FIG. 3B). Thus, reducing ADAM 15 levels or blocking ADAM 15 MP function in vitro abrogates VEGF A-induced endothelial cell proliferation and survival under serum deprivation. This data is consistent with the observed reduction in endothelial cell proliferation in vessel stalks of retinas treated with antibodies to the ADAM 15 MP domain.

Example 5

ADAM 15 is Necessary for VEGF Signalling to Akt

To gain insight into the mechanism of ADAM 15 dependent regulation of EC proliferation and survival, we decided to analyse possible direct interactions with VEGFR2 and effects on VEGF A signalling. We previously showed that VEGFR2 signalling to the MAP kinase pathway was enhanced by its association with the integrin $\alpha_5\beta_1$.

Figure 4:
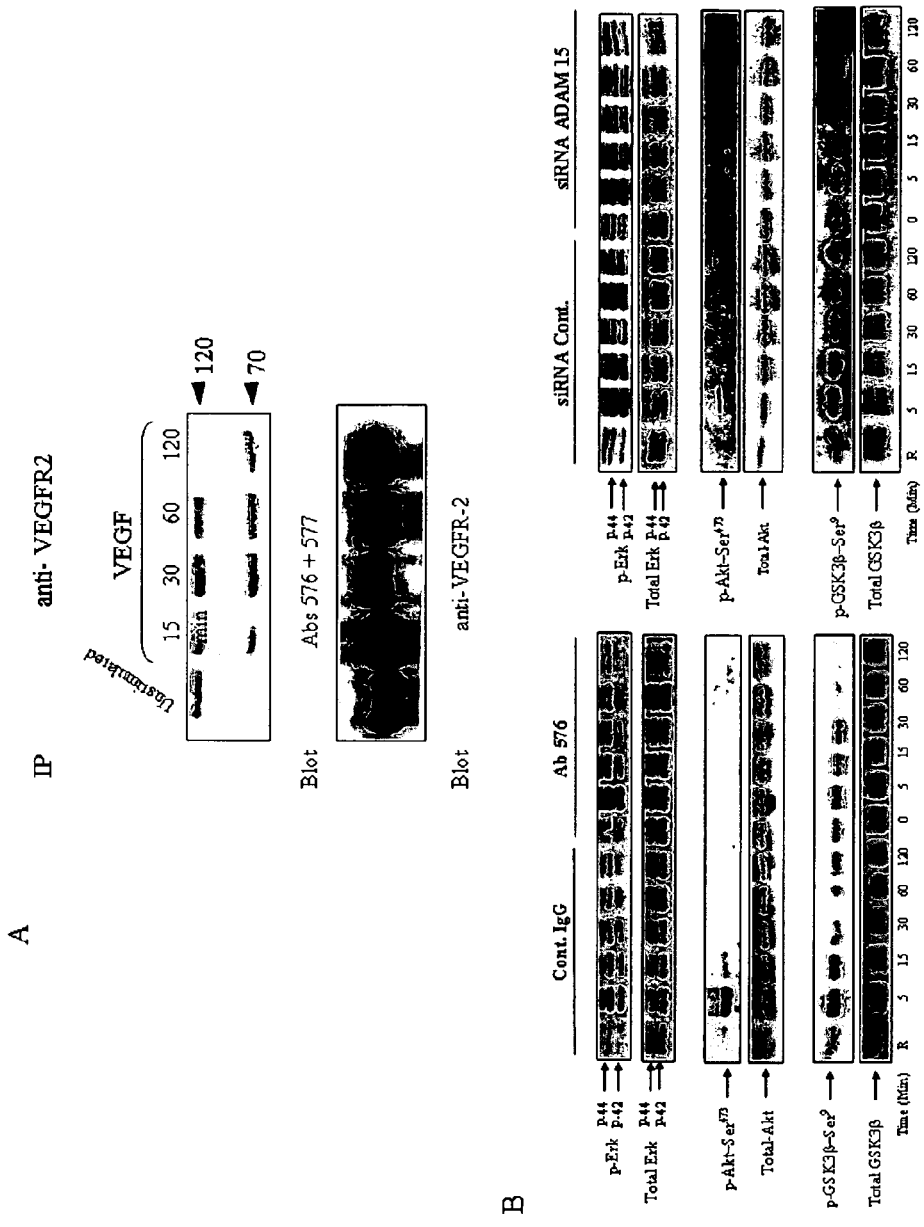
FIG. 4 illustrates the importance of ADAM 15 for VEGF signalling to Akt.

FIG. 4 shows ADAM 15 is important for VEGF signalling to Akt. Panel A VEGF increased ADAM 15 association with VEGFR2 by co-immunoprecipitation. HMVECs were stimulated with VEGF for various time points and lysed. Lysates were then immunoprecipitated with anti-VEGFR2 antibodies. Panel B HMVEC monolayers were treated with Ab 576 or control IgG (left panel) or ADAM 15 siRNA or control siRNA (right panel) and stimulated with VEGF for various periods (0-120 min). Cells were lysed and analysed by SDS-PAGE and Western blotting using the phospho-specific antibodies shown. Blots were then stripped and probed with antigen specific antibodies to assess loading. The results are representative blots from three experiments giving similar results.

Co-immunopreciptation analysis now showed that also ADAM 15 physically associates with VEGFR2, and that this interactions is transiently increased following VEGF stimulation (FIG. 4A). Immunoprecipitation of VEGR2 from non-stimulated EC lysates co-precipitated a 120 kDa antigen reactive to ADAM 15 antibodies, which corresponds to the inactive precursor. Following VEGF stimulation, an increase in VEGFR2 associated ADAM 15 precursor occurred peaking at 30 min and diminishing by 120 min. Concomitantly, the appearance of a 75 kDa antigen corresponding to the active form of ADAM 15 was observed to associate with VEGFR2 and this species remained associated with VEGFR2 even at 120 min post stimulation. These results indicate that upon VEGF stimulation, ADAM 15 association with VEGFR2 increases and this process is accompanied by an activation of the MP domain by proteolytic removal of the prodomain.

To investigate whether and how this association with ADAM 15 modulates VEGFR2 downstream signalling, we studied the activation of two major effectors of VEGFR-2 namely MAP kinases Erk 1/2 and the serine/threonine kinase Akt (FIG. 4 B). Stimulation of cells treated with ADAM 15 MP domain antibodies (left panel) or ADAM 15 siRNA (right panel) both showed similar patterns of Erk1/2 phosphorylation over a 2 hour time course with a biphasic response peaking at approx. 5 min and again at 60 min. Significantly, there was no discernible difference in the magnitude of Erk 1/2 phosphorylation between control and ADAM 15 impaired samples indicating that VEGF signalling to effectors of the MAP kinase pathway was not significantly affected by loss of ADAM 15 function. In contrast, stimulation of cells treated with ADAM 15 MP domain antibodies or ADAM 15 siRNA both promoted a severe impairment of Akt phosphorylation on $Ser^{473}$. Impairment of Akt activation was confirmed by assessing the phosphorylation of the down stream substrate GSK 3β. Phosphorylation of GSK 3β on $Ser^9$ was also significantly reduced (approx. 50%) in ADAM 15 impaired cells compared with control cells after stimulation with VEGF. Unlike Akt phosphorylation, GSK 3β phosphorylation was not fully inhibited as GSK 3β is also regulated by other upstream effectors such as PKC. Therefore, loss of ADAM 15 function appears to significantly impair VEGF signalling to effectors of the PI3 kinase pathway without altering the efficacy of signal transduction to effectors of the MAP kinase pathway. These studies are consistent with the functional data obtained from both in vivo and in vitro assays establishing that VEGF A induced proliferation is inhibited in cells where ADAM 15 function is impaired since previous work has established this pathway as essential for EC proliferation (Qi et al., 1999). The loss of VEGF signalling to Akt in cells treated with siRNA for ADAM 15 is also consistent with the inability of VEGF A to rescue these cells from apoptosis induced by serum deprivation.

Example 6

ADAM 15 Antagonises Endothelial Cell Migration In Vitro

In the retina, endothelial tip cells migrate along a network of astrocytes which produce a Fn matrix (29, 30) and lay down VEGF gradients through heparin-binding VEGF isoforms (3). Blocking ADAM 15 MP function in vivo did not reveal significant defects in the advancement of the sprouting front over the astrocytic network, suggesting that ADAM 15 may not be required for tip cell migration stimulated by VEGF on Fn. However, we previously showed in vitro that VEGF A, in the presence of a Fn matrix, promoted an enhanced migration response which was coupled predominantly to the MAP kinase pathway (24). To directly assess whether ADAM 15 affects EC migration in this context, we used a modified Boyden chamber chemotaxis assay supplemented with a Fn matrix.

Figure 5:
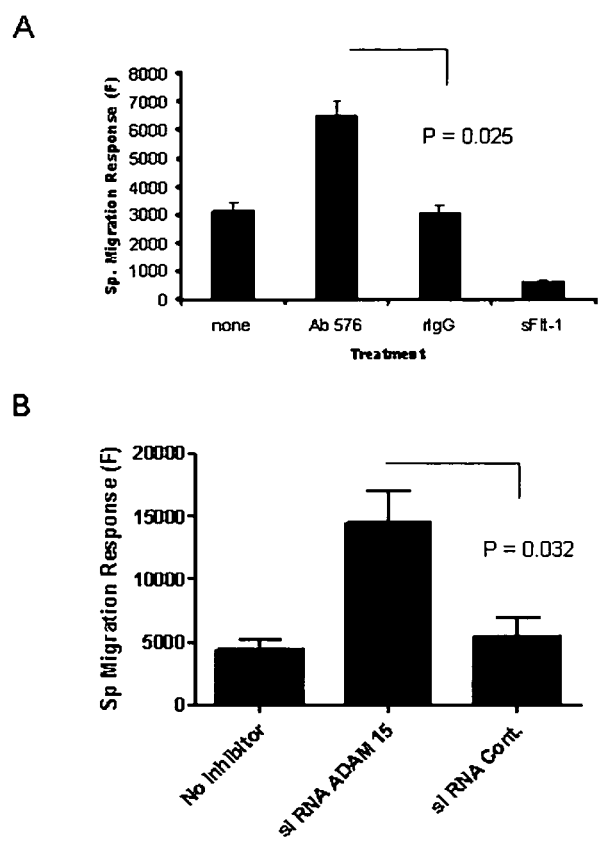
FIG. 5 illustrates non-limiting embodiments of ADAM 15 antagonism that enhances endothelial cell migration in vitro.

FIG. 5 shows antagonism of ADAM 15 enhances endothelial cell migration in vitro. Panel A-Calcein AM loaded HMVECs were pre-incubated with and without Ab's 576 and 577 for 60 min at room temperature prior to stimulation with VEGF-FN complexes in a modified Boyden chamber assay. The results shown is a representative experiment of four similar assays giving similar results.
Panel B-RNA interference of ADAM 15. HMVECs were transiently transfected with ADAM 15 specific si RNA and a scrambled siRNA control. ADAM 15 expression was maximally suppressed at 36 hours post-transfection at which point the migration assay was performed (n=2). The data are expressed as specific migration after subtraction of background migration.

Unexpectedly, cell migration towards VEGF A was elevated (approx. 2-fold) following treatment of cells with Ab 576 (or Ab 577 not shown) (FIG. 5A). Migration was unchanged by treatment with control IgG, but was strongly inhibited by co-administration of the VEGF A inhibitor sflt-1 (soluble VEGFR1). Down regulation of ADAM 15 using ADAM 15 siRNA (FIG. 5B) also enhanced cell migration to a similar extent as the MP domain antibodies whereas control siRNA showed no significant effect. Baseline unstimulated (haptotactic) migration of ADAM 15 siRNA and control siRNA treated ECs were of similar magnitude (data not shown). Therefore, in contrast to EC proliferation and survival, impairing ADAM 15 function or expression did not diminish EC migration in response to VEGF A but rather promoted an enhanced response in vitro.

Example 7

ADAM 15 Negatively Regulates the Plasminogen Activation System by Processing uPAR The observation that VEGF A-induced EC proliferation, survival and migration are differentially affected by blocking ADAM 15 function in vitro suggested that ADAM 15 may modulate the different VEGF responses via distinct mechanisms. Furthermore, the absence of any significant effect upon Erk 1/2 phosphorylation in response to VEGF A in ADAM 15 impaired cells suggested that a non-signal transduction mechanism may underlie the increased EC migration observed in vitro. Prager et al recently showed that VEGFR2 at the leading edge of migrating cells associates with uPAR and that VEGF stimulation induced pro-urokinase activation in ECs (31, 32). We, therefore, decided to examine the effect of ADAM 15 impairment on urokinase activity in ECs.

Figure 6:
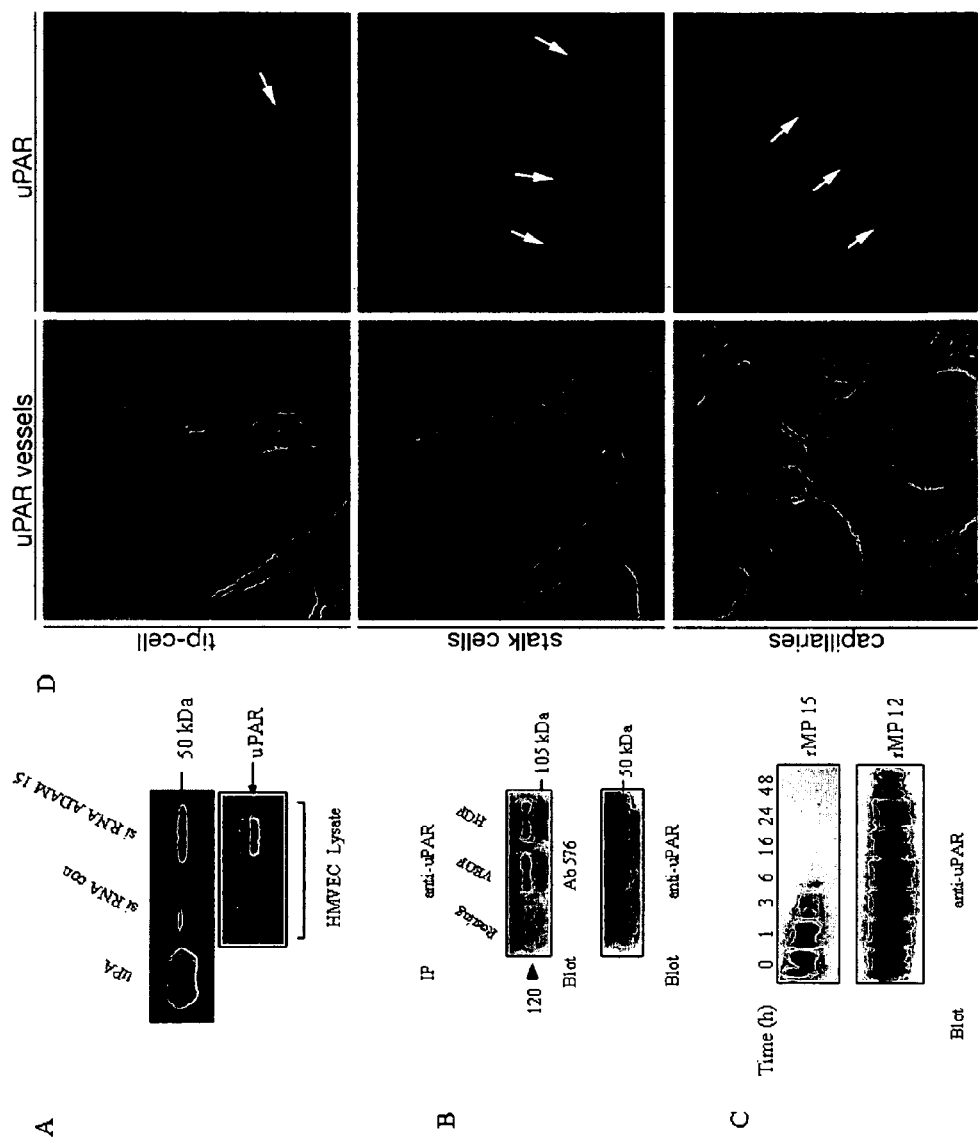
FIG. 6 illustrates non-limiting embodiments of targeted proteolysis of uPAR in endothelial cells by ADAM 15.

FIG. 6 shows targeted proteolysis of uPAR in endothelial cells by ADAM 15. Panel A Casein zymograhic analysis of HMVEC lysates treated with control and ADAM 15 siRNAs. Bottom-analysis of uPAR antigen levels in these lysates by Western blotting. Panel B—VEGF A induces ADAM 15 association with uPAR. HMVECs were stimulated with VEGF A for 30 min and then lysed. Lysates were immunoprecipitated with anti-uPAR antibodies. Immunoprecipitates were analysed by Western blotting probing with Abs 576 and/or 577. Panel C—Degradation of soluble uPAR in a cell free system by recombinant ADAM 15 MP domain. Soluble recombinant uPAR (10 ug) was incubated with recombinant ADAM 15 MP domain (10-50 ng) or recombinant ADAM 12 MP domain (10-50 ng) for various time points and then analysed by Western blotting using an anti-uPAR monoclonal antibody. Panel D Confocal images of whole-mounts of normal P5 retinas double labelled for isolectin (black in left panel) and uPAR (red in left and right panels). Some uPAR is present in tip-cells (top row, arrow), however uPAR is predominantly found in endothelial stalk cells (middle row, arrows) and further back in the capillary plexus (bottom row, arrows).

Plasminogen/casein zymography showed approx. 5-fold increased urokinase activity in lysates of ADAM 15 siRNA compared to control siRNA transfected EC (FIG. 6A top panel). Western blot analysis also showed a corresponding approx. 5-fold increase in uPAR protein levels (FIG. 6A bottom panel). These results suggested that uPAR could be a physiological target for the ADAM 15 metalloprotease activity. Since previous work has shown that uPAR associates with VEGFR2 following VEGF stimulation (32), we examined if ADAM 15, likewise, associated with uPAR. Indeed, we detected co-immunoprecipitation of uPAR and ADAM 15 in lysates of unstimulated cells and this association was increased approx. 3-fold following VEGF A stimulation (FIG. 6B). Stimulation of cells with HGF also promoted uPAR-ADAM 15 association but not to the same extent as VEGF A. To confirm that ADAM 15 MP domain has intrinsic uPAR processing activity, we performed an in vitro substrate-protease reaction. We incubated either recombinant ADAM 15 or ADAM 12 MP domains with recombinant uPAR in vitro at similar enzyme-substrate ratios and assessed the presence of the integrity of an epitope for a uPAR specific monoclonal antibody over a period of 48 hours as a measure of uPAR proteolytic processing (FIG. 6C). The MP domain of ADAM 15 was significantly more reactive towards the cleavage of the uPAR epitope compared to the MP domain of ADAM 12 suggesting that uPAR may indeed be a physiological substrate for ADAM 15 MP activity. Normal vessels of the retina stained with a polyclonal anti-uPAR antibody showed a distinct punctuate labelling located to the EC bodies in the developing vascular plexus. The staining pattern also showed that uPAR expression was predominantly localised to vessel stalk cells and capillaries compared with tip cells (FIG. 6D), consistent with the observation that treatment of retinas with ADAM 15 MP domain antibodies altered capillary morphology predominantly (FIG. 2).

To further test the hypothesis that ADAM 15 targets uPAR for proteolysis, we over-expressed ADAM 15 in a high uPAR expressing cell line and assayed the effects on uPAR surface expression and urokinase activity. A screen of high uPAR expressing cell lines with Ab 576 showed that U937 cells did not express detectable levels of ADAM 15 antigen (FIG. 1E middle panel); these were therefore selected for the analysis. Stable ADAM 15 transfectants were generated that expressed ADAM 15 at levels comparable to microvessel ECs (FIG. 1F and data not shown). uPAR surface expression and antigen levels were measured in these cells in comparison to control cells (FIG. 7).

Figure 7:
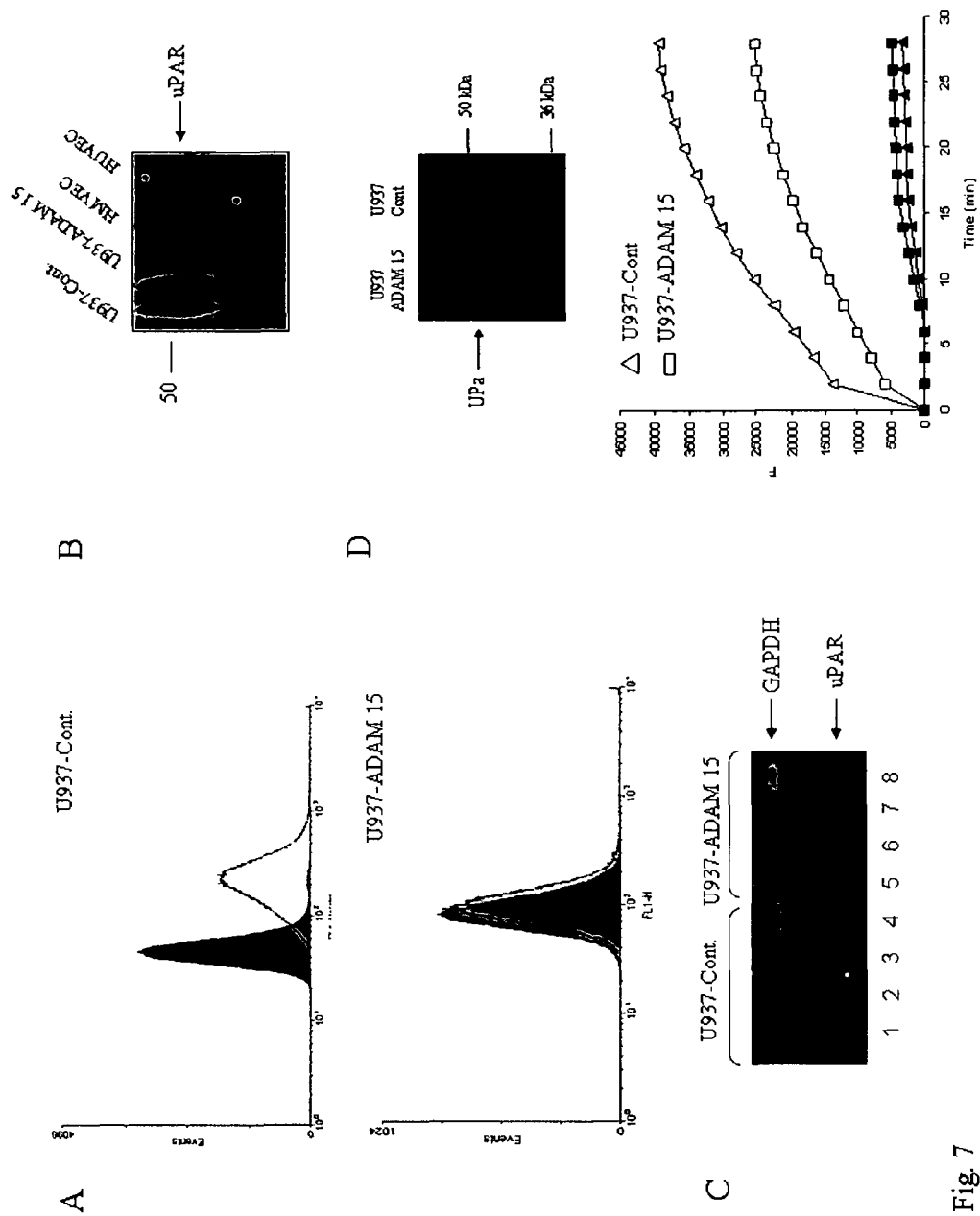
FIG. 7 illustrates non-limiting embodiments of loss of uPAR and urokinase activity in ADAM 15 transfected U937 cells.

FIG. 7 shows loss of uPAR and urokinase activity in ADAM 15 transfected U937 cells. Panel A—Stable ADAM 15 transfected U937 cells were established as described in the materials and methods. Both control, non-transfected and ADAM 15 transfected cells were stained with a uPAR primary monoclonal antibody followed by staining with FITC anti-mouse conjugate. Samples were analysed by FACs. Data is presented as histograms of number of events against with background labelling (no primary antibody) shaded and ADAM 15 labelled samples.

Panel B Cell lysates (40 μg per lane) as shown were analysed by SDS-PAGE and Western blotting probing with a polyclonal anti-uPAR antibody. Blots were developed by Chemiluminescence.

Panel C Total RNA was extracted from control transfected and ADAM 15 transfected U937 cells and semi-quantitative PCR was performed with uPAR and GAPDH specific primer sets. Total RNA template used were 10 ng (lanes 1, 3, 6 and 7) and 50 ng (lanes 2, 4, 5, and 8).

Panel D Caesin/Lys-plasmingen zymograhic analysis of cell lysates from ADAM 15 and control transfected U937 cells. Arrow marks zone of lysis for uPA activity. Whole cell uPA activity assay. ADAM 15 (□/■) and control (Δ/▲) non-transfected U937 cells were incubated with a uPA-specific fluorescent substrate in the presence (filled symbols) or absence (open symbols) of PAI-1. Peptide hydrolysis was measured by an increase in fluorescence over a 30 min duration. Each point was performed in quadruplicate with SE less than 10%. The experiment is a representative experiment performed three times with highly similar results.

While control cells showed high uPAR surface expression (FIG. 7A) and uPAR antigen (FIG. 7B), ADAM 15 transfected cells showed severely (approx. 90%) diminished uPAR surface expression and antigen levels. uPAR mRNA levels were not affected by ADAM 15 expression (FIG. 7C). Furthermore, urokinase activity assessed by casein zymography (FIG. 7D top panel) and specific peptide substrate hydrolysis (FIG. 7D bottom panel), was decreased approx. 3-5 fold in ADAM 15 transfected U937 compared to control U937 cells. Taken together, these studies illustrate that ADAM 15 MP activity is involved in the down regulation of the plasminogen activation pathway in ECs through the proteolytic processing of surface uPAR. Consequently, the impairment of ADAM 15 function in ECs leads to enhanced plasminogen activation consistent with the enhanced migratory responses induced by VEGF A in vitro.

FIG. 8. shows the human ADAM 15 amino acid precursor sequence (AAC50404).

REFERENCES

1. Gerhardt, H., and Betsholtz, C. 2005. How do endothelial cells orientate? *Exs:* 3-15.
2. Ruhrberg, C., Gerhardt, H., Golding, M., Watson, R., Ioannidou, S., Fujisawa, H., Betsholtz, C., and Shima, D. T. 2002. Spatially restricted patterning cues provided by heparin-binding VEGF-A control blood vessel branching morphogenesis. *Genes Dev* 16:2684-2698.
3. Gerhardt, H., Golding, M., Fruttiger, M., Ruhrberg, C., Lundkvist, A., Abramsson, A., Jeltsch, M., Mitchell, C., Alitalo, K., Shima, D., et al. 2003. VEGF guides angiogenic sprouting utilizing endothelial tip cell filopodia. *J Cell Biol* 161:1163-1177.
4. Miralem, T., Steinberg, R., Price, D., and Avraham, H. 2001. VEGF(165) requires extracellular matrix components to induce mitogenic effects and migratory response in breast cancer cells. *Oncogene* 20:5511-5524.
5. Wijelath, E. S., Rahman, S., Murray, J., Patel, Y., Savidge, G., and Sobel, M. 2004. Fibronectin promotes VEGF-induced CD34 cell differentiation into endothelial cells. *J Vasc Surg* 39:655-660.
6. Zhang, X., Groopman, J. E., and Wang, J. F. 2005. Extracellular matrix regulates endothelial functions through interaction of VEGFR-3 and integrin alpha5beta1. *J Cell Physiol* 202:205-214.
7. Wijelath, E. S., Rahman, S., Namekata, M., Murray, J., Nishimura, T., Mostafavi-Pour, Z., Patel, Y., Suda, Y., Humphries, M. J., and Sobel, M. 2006. Heparin-II Domain of Fibronectin Is a Vascular Endothelial Growth Factor-Binding Domain. Enhancement of VEGF Biological Activity by a Singular Growth Factor/Matrix Protein Synergism. *Circ Res*.
8. Fong, G. H., Rossant, J., Gertsenstein, M., and Breitman, M. L. 1995. Role of the Flt-1 receptor tyrosine kinase in regulating the assembly of vascular endothelium. *Nature* 376:66-70.
9. Hiratsuka, S., Minowa, O., Kuno, J., Noda, T., and Shibuya, M. 1998. Flt-1 lacking the tyrosine kinase domain is sufficient for normal development and angiogenesis in mice. *Proc Natl Acad Sci USA* 95:9349-9354.
10. Blobel, C. P. 2005. ADAMs: key components in EGFR signalling and development. *Nat Rev Mol Cell Biol* 6:32-43.
11. White, J. M. 2003. ADAMs: modulators of cell-cell and cell-matrix interactions. *Curr Opin Cell Biol* 15:598-606.
12. Yang, P., Baker, K. A., and Hagg, T. 2006. The ADAMs family: coordinators of nervous system development, plasticity and repair. *Prog Neurobiol* 79:73-94.
13. Blobel, C. P. 1997. Metalloprotease-disintegrins: links to cell adhesion and cleavage of TNF alpha and Notch. *Cell* 90:589-592.
14. Lunn, C. A., Fan, X., Dalie, B., Miller, K., Zavodny, P. J., Narula, S. K., and Lundell, D. 1997. Purification of ADAM 10 from bovine spleen as a TNFalpha convertase. *FEBS Lett* 400:333-335.
15. Pan, D., and Rubin, G. M. 1997. Kuzbanian controls proteolytic processing of Notch and mediates lateral inhibition during *Drosophila* and vertebrate neurogenesis. *Cell* 90:271-280.
16. Alfandari, D., Wolfsberg, T. G., White, J. M., and DeSimone, D. W. 1997. ADAM 13: a novel ADAM expressed in somitic mesoderm and neural crest cells during *Xenopus laevis* development. *Dev Biol* 182:314-330.
17. Alfandari, D., Cousin, H., Gaultier, A., Smith, K., White, J. M., Darribere, T., and DeSimone, D. W. 2001. *Xenopus* ADAM 13 is a metalloprotease required for cranial neural crest-cell migration. *Curr Biol* 11:918-930.
18. Aktas, B., Pozgajova, M., Bergmeier, W., Sunnarborg, S., Offermanns, S., Lee, D., Wagner, D. D., and Nieswandt, B. 2005. Aspirin induces platelet receptor shedding via ADAM17 (TACE). *J Biol Chem* 280:39716-39722.
19. Herren, B., Raines, E. W., and Ross, R. 1997. Expression of a disintegrin-like protein in cultured human vascular cells and in vivo. *Faseb J* 11:173-180.
20. Kratzschmar, J., Lum, L., and Blobel, C. P. 1996. Metargidin, a membrane-anchored metalloprotease-disintegrin protein with an RGD integrin binding sequence. *J Biol Chem* 271:4593-4596.
21. Ham, C., Levkau, B., Raines, E. W., and Herren, B. 2002. ADAM15 is an adherens junction molecule whose surface expression can be driven by VE-cadherin. *Exp Cell Res* 279:239-247.
22. Horiuchi, K., Weskamp, G., Lum, L., Hammes, H. P., Cai, H., Brodie, T. A., Ludwig, T., Chiusaroli, R., Baron, R., Preissner, K. T., et al. 2003. Potential role for ADAM15 in pathological neovascularization in mice. *Mol Cell Biol* 23:5614-5624.
23. Rahman, S., Patel, Y., Murray, J., Patel, K. V., Sumathipala, R., Sobel, M., and Wijelath, E. S. 2005. Novel hepatocyte growth factor (HGF) binding domains on fibronectin and vitronectin coordinate a distinct and amplified Met-integrin induced signalling pathway in endothelial cells. *BMC Cell Biol* 6:8.

24. Wijelath, E. S., Murray, J., Rahman, S., Patel, Y., Ishida, A., Strand, K., Aziz, S., Cardona, C., Hammond, W. P., Savidge, G. F., et al. 2002. Novel vascular endothelial growth factor binding domains of fibronectin enhance vascular endothelial growth factor biological activity. *Circ Res* 91:25-31.

25. Bass, R., Werner, F., Odintsova, E., Sugiura, T., Berditchevski, F., and Ellis, V. 2005. Regulation of urokinase receptor proteolytic function by the tetraspanin CD82. *J Biol Chem* 280:14811-14818.

26. Cirilli, M., Gallina, C., Gavuzzo, E., Giordano, C., Gomis-Ruth, F. X., Gorini, B., Kress, L. F., Mazza, F., Paradisi, M. P., Pochetti, G., et al. 1997. 2 angstrom X-ray structure of adamalysin II complexed with a peptide phosphonate inhibitor adopting a retro-binding mode. *FEBS Lett* 418:319-322.

27. Davies, M. H., Eubanks, J. P., and Powers, M. R. 2006. Microglia and macrophages are increased in response to ischemia-induced retinopathy in the mouse retina. *Mol Vis* 12:467-477.

28. Qi, J. H., Matsumoto, T., Huang, K., Olausson, K., Christofferson, R., and Claesson-Welsh, L. 1999. Phosphoinositide 3 kinase is critical for survival, mitogenesis and migration but not for differentiation of endothelial cells. *Angiogenesis* 3:371-380.

29. Uemura, A., Kusuhara, S., Wiegand, S. J., Yu, R. T., and Nishikawa, S. 2006. Tlx acts as a proangiogenic switch by regulating extracellular assembly of fibronectin matrices in retinal astrocytes. *J Clin Invest* 116:369-377.

30. Jiang, B., Liou, G. I., Behzadian, M. A., and Caldwell, R. B. 1994. Astrocytes modulate retinal vasculogenesis: effects on fibronectin expression. *J Cell Sci* 107 (Pt 9):2499-2508.

31. Prager, G. W., Breuss, J. M., Steurer, S., Olcaydu, D., Mihaly, J., Brunner, P. M., Stockinger, H., and Binder, B. R. 2004. Vascular endothelial growth factor receptor-2-induced initial endothelial cell migration depends on the presence of the urokinase receptor. *Circ Res* 94:1562-1570.

32. Prager, G. W., Breuss, J. M., Steurer, S., Mihaly, J., and Binder, B. R. 2004. Vascular endothelial growth factor (VEGF) induces rapid prourokinase (pro-uPA) activation on the surface of endothelial cells. *Blood* 103:955-962.

33. Stalmans, I., Ng, Y. S., Rohan, R., Fruttiger, M., Bouche, A., Yuce, A., Fujisawa, H., Hermans, B., Shani, M., Jansen, S., et al. 2002. Arteriolar and venular patterning in retinas of mice selectively expressing VEGF isoforms. *J Clin Invest* 109:327-336.

34. Takahashi, T., and Shibuya, M. 1997. The 230 kDa mature form of KDR/Flk-1 (VEGF receptor-2) activates the PLC-gamma pathway and partially induces mitotic signals in NIH3T3 fibroblasts. *Oncogene* 14:2079-2089.

35. Gerber, H. P., McMurtrey, A., Kowalski, J., Yan, M., Keyt, B. A., Dixit, V., and Ferrara, N. 1998. Vascular endothelial growth factor regulates endothelial cell survival through the phosphatidylinositol 3'-kinase/Akt signal transduction pathway. Requirement for Flk-1/KDR activation. *J Biol Chem* 273:30336-30343.

36. Primo, L., di Blasio, L., Roca, C., Droetto, S., Piva, R., Schaffhausen, B., and Bussolino, F. 2007. Essential role of PDK1 in regulating endothelial cell migration. *J Cell Biol* 176:1035-1047.

37. Matsumoto, T., Bohman, S., Dixelius, J., Berge, T., Dimberg, A., Magnusson, P., Wang, L., Wikner, C., Qi, J. H., Wernstedt, C., et al. 2005. VEGF receptor-2 Y951 signaling and a role for the adapter molecule TSAd in tumor angiogenesis. *Embo J* 24:2342-2353.

38. Yamaoka-Tojo, M., Tojo, T., Kim, H. W., Hilenski, L., Patrushev, N. A., Zhang, L., Fukai, T., and Ushio-Fukai, M. 2006. IQGAP1 mediates VE-cadherin-based cell-cell contacts and VEGF signaling at adherence junctions linked to angiogenesis. *Arterioscler Thromb Vasc Biol* 26:1991-1997.

39. Laramee, M., Chabot, C., Cloutier, M., Stenne, R., Holgado-Madruga, M., Wong, A. J., and Royal, I. 2007. The scaffolding adapter Gab1 mediates vascular endothelial growth factor signaling and is required for endothelial cell migration and capillary formation. *J Biol Chem* 282:7758-7769.

40. Dance, M., Montagner, A., Yart, A., Masri, B., Audigier, Y., Perret, B., Salles, J. P., and Raynal, P. 2006. The adaptor protein Gab1 couples the stimulation of vascular endothelial growth factor receptor-2 to the activation of phosphoinositide 3-kinase. *J Biol Chem* 281:23285-23295.

41. Mahabeleshwar, G. H., Feng, W., Phillips, D. R., and Byzova, T. V. 2006. Integrin signaling is critical for pathological angiogenesis. *J Exp Med* 203:2495-2507.

42. Poghosyan, Z., Robbins, S. M., Houslay, M. D., Webster, A., Murphy, G., and Edwards, D. R. 2002. Phosphorylation-dependent interactions between ADAM15 cytoplasmic domain and Src family protein-tyrosine kinases. *J Biol Chem* 277:4999-5007.

43. Nath, D., Slocombe, P. M., Stephens, P. E., Warn, A., Hutchinson, G. R., Yamada, K. M., Docherty, A. J., and Murphy, G. 1999. Interaction of metargidin (ADAM-15) with alphavbeta3 and alpha5beta1 integrins on different haemopoietic cells. *J Cell Sci* 112 (Pt 4):579-587.

44. Zhang, X. P., Kamata, T., Yokoyama, K., Puzon-McLaughlin, W., and Takada, Y. 1998. Specific interaction of the recombinant disintegrin-like domain of MDC-15 (metargidin, ADAM-15) with integrin alphavbeta3. *J Biol Chem* 273:7345-7350.

45. Eto, K., Puzon-McLaughlin, W., Sheppard, D., Sehara-Fujisawa, A., Zhang, X. P., and Takada, Y. 2000. RGD-independent binding of integrin alpha9beta1 to the ADAM-12 and -15 disintegrin domains mediates cell-cell interaction. *J Biol Chem* 275:34922-34930.

46. Carmeliet, P., Lampugnani, M. G., Moons, L., Breviario, F., Compernolle, V., Bono, F., Balconi, G., Spagnuolo, R., Oostuyse, B., Dewerchin, M., et al. 1999. Targeted deficiency or cytosolic truncation of the VE-cadherin gene in mice impairs VEGF-mediated endothelial survival and angiogenesis. *Cell* 98:147-157.

47. Chen, J., Somanath, P. R., Razorenova, O., Chen, W. S., Hay, N., Bornstein, P., and Byzova, T. V. 2005. Akt1 regulates pathological angiogenesis, vascular maturation and permeability in vivo. *Nat Med* 11:1188-1196.

48. Saunders, W. B., Bohnsack, B. L., Faske, J. B., Anthis, N. J., Bayless, K. J., Hirschi, K. K., and Davis, G. E. 2006. Coregulation of vascular tube stabilization by endothelial cell TIMP-2 and pericyte TIMP-3. *J Cell Biol* 175:179-191.

49. Saunders, W. B., Bayless, K. J., and Davis, G. E. 2005. MMP-1 activation by serine proteases and MMP-10 induces human capillary tubular network collapse and regression in 3D collagen matrices. *J Cell Sci* 118:2325-2340.

50. Bajou, K., Masson, V., Gerard, R. D., Schmitt, P. M., Albert, V., Praus, M., Lund, L. R., Frandsen, T. L., Brunner, N., Dano, K., et al. 2001. The plasminogen activator inhibitor PAI-1 controls in vivo tumor vascularization by interaction with proteases, not vitronectin. Implications for antiangiogenic strategies. *J Cell Biol* 152:777-784.

51. Blobel et al. International patent application publication WO2004/024089
52. Rahman et al. Poster entitled "ADAM 15 is a negative regulator of endothelial cell migration induced by VEGF-fibronectin" presented at "Fibronectin, Integrins and Related Molecules" Gordon Research Conference, Jan. 30-Feb. 4, 2005, Ventura Beach Marriott, Ventura, Calif.
53. Bellacosa A, Kumar C C, Di Cristofano A and Testa J R: Activation of AKT kinases in cancer: implications for therapeutic targeting. Adv Cancer Res 94: 29-86, 2005.
54. Ikenoue T, Kanai F, Hikiba Y, et al: Functional analysis of PIK3CA gene mutations in human colorectal cancer. Cancer Res 65: 4562-4567, 2005.
55. Samuels Y, Diaz L A Jr, Schmidt-Kittler O, et al: Mutant PIK3CA promotes cell growth and invasion of human cancer cells. Cancer Cell 7: 561-573, 2005.
56. Samuels Y, Wang Z, Bardelli A, et al: High frequency of mutations of the PIK3CA gene in human cancers. Science 304:554, 2004.
57. Saal L H, Holm K, Maurer M, et al: PIK3CA Mutations correlate with hormone receptors, node metastasis, and ERBB2, and are mutually exclusive with PTEN loss in human breast carcinoma. Cancer Res 65: 2554-2559, 2005.
58. Levine D A, Bogomolniy F, Yee C J, Lash A, Barakat R R, Borgen P I and Boyd J: Frequent mutation of the PIK3CA gene in ovarian and breast cancers. Clin Cancer Res 11: 2875-2878, 2005.
59. Lee J W, Soung Y H, Kim S Y, et al: PIK3CA gene is frequency mutated in breast carcinomas and hepatocellular carcinomas. Oncogene 24: 1477-1480, 2005.
60. Qiu W, Schonleben F, Li X, et al: PIK3CA mutations in head and neck squamous cell carcinoma. Clin Cancer Res 12: 1441-1446, 2006.
61. Busso, N and Hamilton, JA Extracellular coagulation and the plasminogen activator/plasmin system in rheumatoid arthritis. Arthritis Rheum. 46, 2046-2054, 2002.
62. Macri L, Silverstein D, Clark R A. Growth factor binding to the pericellular matrix and its importance in tissue engineering. Adv Drug Deliv Rev. November 10; 59(13):1366-81. (2007).
63. Charrier-Hisamuddin, L., Laboisse, CL, and Merlin, D. ADAM-15: a metalloprotease that mediates inflammation. FASEB J 22, 1-14, 2007.
64. Murphy, G. The ADAMs: signalling scissors in the tumour microenvironment. Nat. Rev. Cancer, 8, 929-941, 2008.

Each of the foregoing patents, patent applications and references that are recited in this application are herein incorporated in their entirety by reference. Having thus described several aspects of embodiments of this invention, it is to be appreciated various alterations, modifications, and improvements will readily occur to those skilled in the art in view of the teachings set forth herein. Such alterations, modifications, and improvements are intended to be part of this disclosure, and are intended to be within the spirit and scope of the invention. Accordingly, the description and drawings are by way of example only.

What is claimed is:

1. An isolated monoclonal antibody or antigen-binding fragment thereof that inhibits neovascularization, wherein the antibody or antigen-binding fragment thereof specifically binds to the catalytic cleft of the ADAM 15 metalloprotease domain and specifically inhibits ADAM 15 metalloprotease activity.

2. The isolated antibody or antigen-binding fragment thereof of claim 1, wherein the antibody or antigen-binding fragment thereof specifically binds to a peptide having an amino acid sequence:

IAHELGHSLGLDHD          (SEQ ID NO: 3)

or a peptide with at least 90% sequence identity to SEQ ID NO: 3.

3. The isolated antibody or antigen-binding fragment thereof of claim 1, wherein the antibody or antigen-binding fragment thereof specifically binds to an epitope on human ADAM 15 polypeptide, wherein the epitope comprises amino acids 346-359 of SEQ ID NO: 1.

4. The isolated antibody or antigen-binding fragment thereof of claim 1, wherein the antibody or antigen-binding fragment thereof is a mouse, humanized, human, recombinant, chimeric, or synthetic antibody or antigen-binding fragment thereof.

5. The isolated antibody or antigen-binding fragment thereof of claim 1, wherein the antibody or antigen-binding fragment thereof is capable of:
   preventing proteolytic cleavage of the urokinase receptor (uPAR) by ADAM 15,
   inhibiting the activation of the phosphoinositol 3 kinase (PI3 kinase) pathway including the Akt kinase (protein kinase B),
   inhibiting the inactivation of glycogen synthase kinase 3 (GSK 3),
   inhibiting cell survival, and/or
   inhibiting endothelial cell proliferation.

6. The isolated antibody or antigen-binding fragment of claim 1, wherein the antibody or antigen-binding fragment thereof comprises Fab, Fab1, F(ab')2, scFv, Fv, dsFv, ds-scFv, Fd, dAbs, TandAbs dimers, minibodies, diabodies, multimers thereof, or a bispecific antibody fragment.

7. The isolated antibody or antigen-binding fragment thereof of claim 1, wherein the antibody or antigen-binding fragment thereof specifically binds to an epitope on human ADAM 15 polypeptide,
   wherein the epitope comprises amino acids $His^{352}$, $Ser^{353}$, $Leu^{354}$, $Gly^{355}$, $Leu^{356}$, $Asp^{357}$ and $Asp^{359}$ of SEQ ID NO: 1; or
   wherein the epitope comprises amino acids $Leu^{354}$, $Gly^{355}$, $Leu^{356}$, $Asp^{357}$, $His^{358}$ and $Asp^{359}$ of SEQ ID NO: 1.

* * * * *